United States Patent
Rinker et al.

(10) Patent No.: US 10,138,183 B2
(45) Date of Patent: Nov. 27, 2018

(54) PROCESS AND COMPOSITION FOR INHIBITING THE POLYMERIZATION OF CYCLOPENTADIENE COMPOUNDS

(71) Applicants: Stefanie Rinker, Dorsten (DE); Bettina Ludwig, Marl (DE); Manfred Neumann, Marl (DE); Felix Nissen, Nottuln (DE); Oliver Erpeldinger, Wuelfrath (DE); Phillip R. James, Tenby (GB); Peter Watkins, West Berkshire (GB)

(72) Inventors: Stefanie Rinker, Dorsten (DE); Bettina Ludwig, Marl (DE); Manfred Neumann, Marl (DE); Felix Nissen, Nottuln (DE); Oliver Erpeldinger, Wuelfrath (DE); Phillip R. James, Tenby (GB); Peter Watkins, West Berkshire (GB)

(73) Assignee: Evonik Degussa GmbH, Essen (DE)

( * ) Notice: Subject to any disclaimer, the term of this patent is extended or adjusted under 35 U.S.C. 154(b) by 200 days.

(21) Appl. No.: 15/137,900

(22) Filed: Apr. 25, 2016

(65) Prior Publication Data

US 2016/0237008 A1    Aug. 18, 2016

Related U.S. Application Data

(63) Continuation of application No. 14/217,588, filed on Mar. 18, 2014, now Pat. No. 9,493,382.

(30) Foreign Application Priority Data

Mar. 20, 2013    (DE) .................. 10 2013 204 950

(51) Int. Cl.
*C07C 7/20* (2006.01)
*C09K 15/08* (2006.01)
(Continued)

(52) U.S. Cl.
CPC ................ *C07C 7/20* (2013.01); *C09K 15/08* (2013.01); *C09K 15/20* (2013.01); *C07C 7/148* (2013.01);
(Continued)

(58) Field of Classification Search
CPC ............ C07C 7/20; C07C 7/148; C08F 12/00
See application file for complete search history.

(56) References Cited

U.S. PATENT DOCUMENTS 3,061,586 A    10/1962   Thompson
3,530,193 A     9/1970   Starnes, Jr.
(Continued)

FOREIGN PATENT DOCUMENTS

CA    2 642 560 A1    5/2009
CN    1699311 A      11/2005
(Continued)

OTHER PUBLICATIONS

Office Action dated May 31, 2017 in Malaysian Patent Application No. PI 2014000772.
(Continued)

*Primary Examiner* — Youngsul Jeong
(74) *Attorney, Agent, or Firm* — Oblon, McClelland, Maier & Neustadt, L.L.P.

(57) ABSTRACT

A process for inhibiting the polymerization of cyclopentadiene compounds (B) by contacting the cyclopentadiene
(Continued)

compound with a quinone methide compound (A) of structure (I),

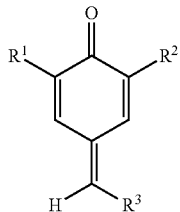

Compositions (AB) comprising (A) and (B) are also provided.

15 Claims, 2 Drawing Sheets

(51) Int. Cl.
    *C09K 15/20*     (2006.01)
    *C07C 7/148*     (2006.01)

(52) U.S. Cl.
    CPC ...... *C07C 2601/10* (2017.05); *C07C 2603/68* (2017.05)

(56) References Cited

U.S. PATENT DOCUMENTS

| | | | |
|---|---|---|---|
| 4,003,800 | A | 1/1977 | Bacha et al. |
| 4,040,911 | A | 8/1977 | Bacha et al. |
| 4,654,451 | A | 3/1987 | Miller et al. |
| 5,616,774 | A | 4/1997 | Evans et al. |
| 5,670,692 | A | 9/1997 | Nesvadba et al. |
| 7,030,279 | B1 | 4/2006 | Tanielyan et al. |
| 7,045,647 | B2 | 5/2006 | Benage |
| 7,046,647 | B2 | 5/2006 | Oba et al. |
| 8,128,804 | B2 | 3/2012 | Weyler et al. |
| 8,212,081 | B2 | 7/2012 | Rinker et al. |
| 2003/0205452 | A1 | 11/2003 | Merrill |
| 2004/0034247 | A1 | 2/2004 | Eldin |
| 2005/0027150 | A1 | 2/2005 | Eldin et al. |
| 2005/0256312 | A1 | 11/2005 | Osterholt et al. |
| 2006/0020089 | A1 | 1/2006 | Merrill |
| 2006/0283699 | A1 | 12/2006 | Ma et al. |
| 2007/0208204 | A1 | 9/2007 | Meyer et al. |
| 2009/0114878 | A1* | 5/2009 | Weyler ............... C07C 7/20 252/182.29 |
| 2010/0267992 | A1 | 10/2010 | Rinker et al. |
| 2012/0101295 | A1 | 4/2012 | Weyler et al. |

FOREIGN PATENT DOCUMENTS

| | | |
|---|---|---|
| CN | 1907927 A | 2/2007 |
| CN | 101104573 A | 1/2008 |
| CN | 101423449 A | 5/2009 |
| DE | 694 19 662 T2 | 1/2000 |
| DE | 696 09 110 T2 | 3/2001 |
| EP | 0 626 377 A1 | 11/1994 |
| EP | 0 737 659 B1 | 7/2000 |
| EP | 0 737 660 B1 | 8/2002 |
| EP | 2 055 691 A1 | 5/2009 |
| JP | 61-165338 A | 7/1986 |
| JP | 61-165338 A | 7/1986 |
| JP | 9-176215 A | 7/1997 |
| JP | 2003-515656 A | 5/2003 |
| JP | 2004-511569 A | 4/2004 |
| JP | 2004-513985 A | 5/2004 |
| JP | 2011-256142 A | 12/2011 |
| WO | WO 99/48896 A1 | 9/1999 |
| WO | WO 01/40404 A1 | 6/2001 |
| WO | WO01/47844 A1 * | 7/2001 |
| WO | WO 01/47844 A1 | 7/2001 |
| WO | WO 02/33025 A2 | 4/2002 |
| WO | WO 02/33026 A1 | 4/2002 |
| WO | WO 2004/026995 A1 | 4/2004 |
| WO | WO 2008/067012 A1 | 6/2008 |
| WO | WO 2010/078096 A1 | 7/2010 |

OTHER PUBLICATIONS

European Search Report dated Feb. 9, 2009 in EP 08 16 5122 (with English translation of category of cited documents).
C.M. Orlando, "Quinone Methide Chemistry. The Benzylic Oxidative Methoxylation of 2, 6-Di-tert-butyl-p-cresol", J. Org. Chem. vol. 35, No. 11, XP-002514061 , 1970, pp. 3714-3717.
Von Eugen Muller, et al., "Instabile Aroxyle", Justus Liebigs Annalen Der Chemie, Verlag Chemie GMBH, Weinheim, De, vol. 645, XP-009096429, Jan. 1, 1961, pp. 66-78.
A. A. Yassin, et al. , "The Mechanisms of Retardation and Inhibition in Radical Polymerizations by Quinones", European Polymer Journal, vol. 9, No. 7, XP-023321771, Jul. 1, 1973, pp. 657-667.
Taiwanese Office Action dated Jun. 20, 2013 in Taiwanese Patent Application No. 097141190 (English translation only).
Japanese Office Action dated Jun. 24, 2013 in Patent Application No. 2008-282889 (German Translation only).
R.E. Winkler, et al., "*Inhibition of the Thermal Polymerization of Styrene by* N-*Phenyl-*N'-*Isopropyl-*p-*Phenylenediamine*", J. Polym. Sci. Polym. Chem. Ed., vol. 26, 1988, pp. 2853-2858.
European Search Report dated Jul. 2, 2014 in Patent Application No. 14160170.8 with English Translation of Category of Cited Documents.
Written Opinion and Search Report dated Mar. 20, 2015 in Patent Application No. 10201400699R.
Maria M. Toteva, et al., "The generation and reactions of quinone methides" Advances in Physical Organic Chemistry, vol. 45, Jan. 1, 2011, pp. 39-91.
Palmova et al., 2001, Experimental and Modeling Studies of Oligomerization and Copolymerization of Dicyclopentadien, Chemical Engineering Science, vol. 56, pp. 927-935.

\* cited by examiner

PROCESS AND COMPOSITION FOR INHIBITING THE POLYMERIZATION OF CYCLOPENTADIENE COMPOUNDS

CROSS REFERENCE TO RELATED APPLICATIONS

This application is a divisional of U.S. application Ser. No. 14/217,588 filed on Mar. 18, 2014, claiming priority to German Application No. 102013204950.1, filed Mar. 20, 2013, the disclosure of which is incorporated herein by reference in its entirety.

BACKGROUND OF THE INVENTION

This invention relates to a composition comprising quinone methides useful for stabilizing cyclopentadiene compounds such as, for example, cyclopentadiene and dicyclopentadiene. It relates to a process for inhibiting the polymerization of cyclopentadiene compounds. Application may be possible in all process streams comprising cyclopentadiene compounds.

DESCRIPTION OF THE BACKGROUND

Cyclopentadiene (=CPD) is a very reactive molecule which dimerizes to dicyclopentadiene (=DCPD) even at low temperatures, via a Diels-Alder reaction. For this reason the dimeric form is also the commercially available form of cyclopentadiene. The monomer can be restored by a retro-Diels-Alder reaction at high temperatures. The reversible dimerization of CPD to DCPD can thus be described as depicted hereinbelow in reaction equation <1> (the forward reaction from CPD to DCPD is the dimerization, which is preferential at low temperatures; the reverse reaction from DCPD to CPD is the cleavage, which is preferential at high temperatures, i.e. T>155° C.):

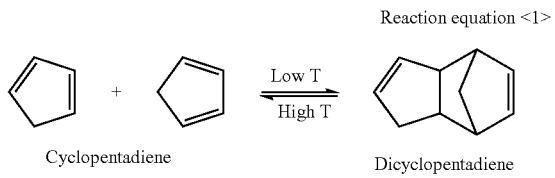 [SMILES: C1=CCC=C1 ; C1=CCC=C1 ; C1=CC2C3C=CC(C3)C2C1]

Reaction equation <1>

Cyclopentadiene       Dicyclopentadiene

However, CDP and DCDP have a tendency to polymerize. This can be explained by various mechanisms. These include inter alia the possibility of further Diels-Alder reactions; on the other hand, free-radical polymerizations also take place. It is also possible to imagine mixed polymerization mechanisms. The Diels-Alder polymerization is shown in reaction equation <2>.

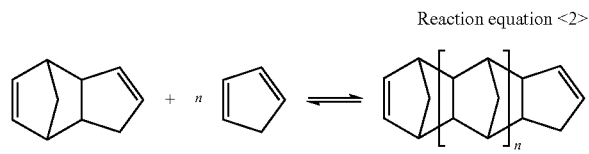

Reaction equation <2>

This high tendency for CPD and its compounds to polymerize can lead to a variety of problems in all (di)cyclopentadiene-containing process streams as well as with the specific production of cyclopentadiene monomer.

Cyclopentadiene compounds such as cyclopentadiene and dicyclopentadiene are thus present in some process streams, for example in pyrolysis gasoline, as secondary components, and can react with themselves or other vinyl-containing monomers in polymerization reactions. These undesired polymerization reactions occur particularly at high temperatures and can lead to deposits in the plants. The consequence of this is a reduced heat transfer and hence a reduced productivity. If the deposits lead to blockages, unscheduled cleaning of the plant has to be carried out, which leads to interruptions in the manufacturing operation. Every outage adds costs due to repair and cleaning, but in particular also due to the manufacturing outage itself. Avoidance of such outages is therefore a constant objective.

The described problems due to undesired polymerization occur not just in process streams comprising cyclopentadiene compounds as secondary compounds, but also and particularly in the production of cyclopentadiene itself. As previously noted, cyclopentadiene is obtained industrially by cleaving ("cracking") dicyclopentadiene (in accordance with the high-T reverse reaction in the above reaction equation <1>). The cracking of dicyclopentadiene can take place not only in the liquid phase but also in the gas phase as described by Z. Cai, B. Shen, W. Liu, Z. Xin, and H. Ling (Energy & Fuels 2009, 23, 4077-4081). Particularly the liquid phase version of cracking is prone to the problem of oligomer deposits. Again, reduced heat transfer, reduced productivity and in the extreme case even blockage of plant components can occur, necessitating shutdowns and cleans. Temperatures of not less than 155° C. are needed to crack dicyclopentadiene to cyclopentadiene. These temperatures lead to the very rapid formation of cyclopentadiene oligomers and polymers, which raise the viscosity and thereby make stirring more difficult, and which form deposits and inhibit effective heat transfer, making the reaction more difficult to carry out and entailing yield losses.

Various strategies are described to control the formation of oligomers in the cracking of dicyclopentadiene. The most widely used option is to add an inert solvent as a bottoms diluent. Long-chain hydrocarbons are used for this in particular. The solvent does not prevent the polymerization, but slows it, by reducing the concentration of the reactive component. The advantage of such use of solvent is that the oligomers formed dissolve in the solvent and so do not form deposits, as a result of which the reaction mixture remains workable. Moreover, using a solvent can be used to shorten the period of thermal exposure. This advantage is described by Ammannati et al. (WO2010/020549). Diphenyl ether is used therein as inert solvent. Robota (DE1951320; GB1261565) describes a cracking process wherein a paraffinic hydrocarbon oil is employed as a solvent.

On the other hand, the employment of an inert solvent entails the disadvantage that a portion of the reactor volume is already occupied by the solvent, so the volume-time yield is reduced by the addition of a solvent.

Another conventionally known method to inhibit undesirable polymerizations is offered by the employment of polymerization inhibitors. This possibility is used particularly to inhibit polymerization in process streams comprising various, partly vinylic, monomers, but also DCPD and CPD.

The following classes of inhibitor have been described for this purpose: nitroxides such as TEMPO derivatives, phenyldiamines, hydroxylamines such as diethylhydroxylamine (abbreviated as "DEHA"), nitroaromatics such as 4,6-dinitro-2-sec-butylphenol (abbreviated as "DNBP"), diphenols such as hydroquinone (abbreviated as "HQ") and p-tert-butylcatechol (abbreviated as "TBC").

Buccolini et al. (WO2001/047844) describe using a combination of nitroxide compounds, in particular TEMPO derivatives and aromatic amines, in particular diphenylamines and phenylenediamines, to inhibit polymerization reactions in hydrocarbon streams. These hydrocarbon streams comprise butadiene and styrene, but may also comprise cyclopentadiene.

Kazuo et al. (JP62167733A & JP62167734A) describe the admixture of hydroxylamines and TEMPO derivatives, respectively, to a reaction mixture, for example of cyclopentadiene and dicyclopentadiene with 1,3-butadiene, to prevent secondary polymerization reactions.

Ammannati et al. (WO2010/020549) describe a process for producing ethylidenenorbornenes wherein dicyclopentadiene is converted into cyclopentadiene in a first step. Various inert solvents can be used here, for example diphenyl ether, diphenylmethane, decalin or a mixture of di- and triaryl ethers. Polymerization inhibitors such as, for example, 4-oxo-2,2,6,6-tetramethylpiperidine N-oxide (abbreviated as "4-oxo-TEMPO") and also tert-butylhydroquinone are additionally used.

Cai et al. (Z. Cai, B. Shen, W. Liu, Z. Xin, H. Ling, *Energy & Fuels* 2009, 23, 4077-4081) describe o-nitrophenol, TBC and DEHA as possible inhibitors. A 3:1 mixture (by weight) of TBC and DEHA is referred to as particularly advantageous.

Cheng et al. (CN101798255) describe polymerization inhibitors useful for removing diolefins from the C5 fraction in a cracking process, specifically in the extraction of 1,3-pentadiene. Sodium nitrite, TBC, DEHA and o-nitrophenol are mentioned as possible polymerization inhibitors.

Ge et al. (CN101104573) describe a process for separating isoprene and cyclopentadiene wherein polymerization inhibitors are employed. The inhibitors employed can be one or more substances selected from o-nitrophenol, TBC, DEHA and dihydroxydihydrocinnamic acid.

Chen et al. (CN102060649) describe a process for producing cyclopentadiene wherein HQ, 2,6-dinitrocresol and/or TBC or phenothiazine (abbreviated as "PTZ") are employed.

Hu et al. (CN1253130) describe a process for removing diolefins from a C5 stream wherein DEHA, TBC or o-nitrophenol can be used as stabilizers.

Lartigue-Peyrou et al. (WO1999/015603) describe mixtures of catechol derivatives and aromatic ethers useful for stabilizing unsaturated compounds, including cyclopentadiene and dicyclopentadiene.

Cocuta et al. (RO93489) describe mixtures of sec-butylphenols and phenylenediamines/tert-butylcatechols capable of inhibiting the polymerization of olefins and diolefins.

However, experiments employing pure cyclopentadiene surprisingly show that most of the conventionally known inhibitors which have also been used inter alia for application in the presence of cyclopentadiene have little if any efficacy when used to prevent the polymerization of cyclopentadiene (see Comparative Examples 1 to 6). This applies for example to the substances described in WO2010/020549, WO2001/047844 and JP62167734, which are efficacious as inhibitors for the polymerization reactions of monomers such as butadiene or styrene (see Comparative Examples 13 to 16). As shown in Comparative Examples 1 to 6, however, these substances fail when used for inhibiting the polymerization of cyclopentadiene. DNBP, for example, was found to have no effect with regard to the polymerization of cyclopentadiene. The TEMPO derivatives likewise have only minimal efficacy.

It was accordingly surprisingly found that conventional inhibitors are not very suitable for preventing the polymerization in CPD or DCPD-containing process streams and are mainly or even exclusively effective as inhibitors of free-radical polymerizations observed with vinyl-containing monomers. The fact that certain substances have been described as generally useful for stabilizing olefinically unsaturated monomers cannot be used, therefore to infer their usefulness for inhibiting the polymerization of cyclopentadiene, dicyclopentadiene or other cyclopentadiene compounds.

It is an object of the present invention to provide a polymerization inhibitor having good activity against undesired polymerizations of dicyclopentadiene and cyclopentadiene. The inhibitor should also work at high to very high temperatures and exhibit an improved performance over the inhibitors previously conventionally employed.

SUMMARY OF THE INVENTION

It has now been found that this object is achieved, utterly surprisingly, by the employment of certain quinone methides [hereinbelow "Compound of structure (I)"]. They have outstanding inhibitory properties with regard to the polymerization of CPD and DCPD, which is surprising in itself because they have hitherto merely been described for inhibiting the polymerization of vinylic monomers (EP2055691A1; EP0737659A1; EP0737660A1, WO2012/173909). It is further surprising that the inhibitory effect of the quinone methides according to the invention is superior to that of the conventionally known CPD and DCPD polymerization inhibitors. The quinone methides according to the invention may be used neat as well as in diluted form. The cyclopentadiene compound can be in pure form or as a component in a process stream.

The invention relates to a composition (AB) comprising (A) and (B), a process for inhibiting the polymerization of (B) which is characterized in that (A) and (B) are brought into contact, and also to the use of (A) for inhibiting the polymerization of (B), wherein (A) is at least one compound of structure (I)

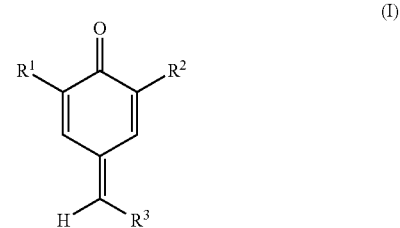

where $R^1$ and $R^2$ are each independently hydrogen, alkyl of 1 to 18 carbon atoms, cycloalkyl of 3 to 15 carbon atoms, aryl of 6 to 15 carbon atoms or phenylalkyl of 7 to 15 carbon atoms;

$R^3$ is —CN, —COOH, —COOR$^4$, —COR$^5$, —OCOR$^6$, —CONR$^7$R$^8$, —PO(OR$^9$)$_2$, —O—R$^{10}$, —S—R$^{11}$, —R$^{12}$, —C≡C—R$^{13}$ or halogen; where $R^4$, $R^5$, $R^6$ are alkyl of 1 to 18 carbon atoms, cycloalkyl of 3 to 12 carbon atoms, aryl of 6 to 10 carbon atoms;

$R^7$ and $R^8$ are each independently hydrogen; alkyl of 1 to 15 carbon atoms which is unsubstituted or substituted with at least one substituent selected from the group consisting of alkylamino having 1 to 4 carbon atoms, dialkylamino having 2 to 8 carbon atoms and hydroxyl; phenylalkyl of 7 to 15 carbon atoms which is unsubstituted or substituted with at least one substituent selected from the group consisting of hydroxyl, alkyl having 1 to 4 carbon atoms, alkylamino having 1 to 4 carbon atoms and dialkylamino having 2 to 8 carbon atoms; aryl of 6 to 10 carbon atoms which is unsubstituted or substituted with at least one substituent selected from the group consisting of alkyl having 1 to 4 carbon atoms, alkylamino having 1 to 4 carbon atoms, dialkylamino having 2 to 8 carbon atoms and hydroxyl; or $NR^7R^8$ is morpholino, piperidino or pyrrolidino;

$R^9$, $R^{10}$, $R^{11}$ are hydrogen; alkyl of 1 to 15 carbon atoms which is unsubstituted or substituted with at least one substituent selected from the group consisting of hydroxyl, dialkylamino, $—OR^{14}$, $—[O(CH_2)_y]_xH$, where x is 1, 2, 3, 4, 5, 6, 7, 8, 9 or 10 and y is 1, 2, 3 or 4 and where $R^{14}$ is alkyl of 1 to 6 carbon atoms;

cycloalkyl of 3 to 15 carbon atoms which is unsubstituted or substituted with at least one substituent selected from the group consisting of hydroxyl, dialkylamino, $—OR^{14}$, $—[O(CH_2)_y]_xH$, where x is 1, 2, 3, 4, 5, 6, 7, 8, 9 or 10 and y is 1, 2, 3 or 4 and where $R^{14}$ is alkyl of 1 to 6 carbon atoms; phenylalkyl of 7 to 15 carbon atoms which is unsubstituted or substituted with at least one substituent selected from the group consisting of hydroxyl, dialkylamino, $—OR^{14}$, $—[O(CH_2)_y]_xH$, where x is 1, 2, 3, 4, 5, 6, 7, 8, 9 or 10 and y is 1, 2, 3 or 4 and where $R^{14}$ is alkyl of 1 to 6 carbon atoms; or aryl of 6 to 15 carbon atoms which is unsubstituted or substituted with at least one substituent selected from the group consisting of hydroxyl, dialkylamino, $—OR^{14}$, $—[O(CH_2)_y]_xH$, where x is 1, 2, 3, 4, 5, 6, 7, 8, 9 or 10 and y is 1, 2, 3 or 4 and where $R^{14}$ is alkyl of 1 to 6 carbon atoms;

$R^{12}$ is 2-pyridyl, 3-pyridyl, 4-pyridyl, 2-thienyl, 3-thienyl, 2-pyrryl, 3-pyrryl, 2-furyl, 3-furyl or aryl of 6 to 15 carbon atoms; wherein the radicals 2-pyridyl, 3-pyridyl, 4-pyridyl, 2-thienyl, 3-thienyl, 2-pyrryl, 3-pyrryl, 2-furyl, 3-furyl or aryl of 6 to 15 carbon atoms are unsubstituted or substituted with at least one substituent selected from the group consisting of hydroxyl, nitro, amino, cyano, carboxyl, aminocarbonyl, halogen, alkyl of 1 to 8 carbon atoms, alkoxy of 1 to 8 carbon atoms, alkylthio of 1 to 8 carbon atoms, alkylamino of 1 to 8 carbon atoms, dialkylamino of 2 to 8 carbon atoms and a carboxylic ester group of 2 to 8 carbon atoms;

$R^{13}$ is hydrogen, alkyl of 1 to 12 carbon atoms, aryl of 6 to 10 carbon atoms, wherein the aryl of 6 to 10 carbon atoms is unsubstituted or substituted with at least one substituent selected from the group consisting of hydroxyl, nitro, amino, cyano, carboxyl, aminocarbonyl, halogen, alkyl of 1 to 8 carbon atoms, alkoxy of 1 to 8 carbon atoms, alkylthio of 1 to 8 carbon atoms, alkylamino of 1 to 8 carbon atoms, dialkylamino of 2 to 8 carbon atoms and a carboxylic ester group of 2 to 8 carbon atoms;

wherein the substituents $R^1$, $R^2$ and $R^3$ are the same or different; and (B) is at least one cyclopentadiene compound.

Figure 1:
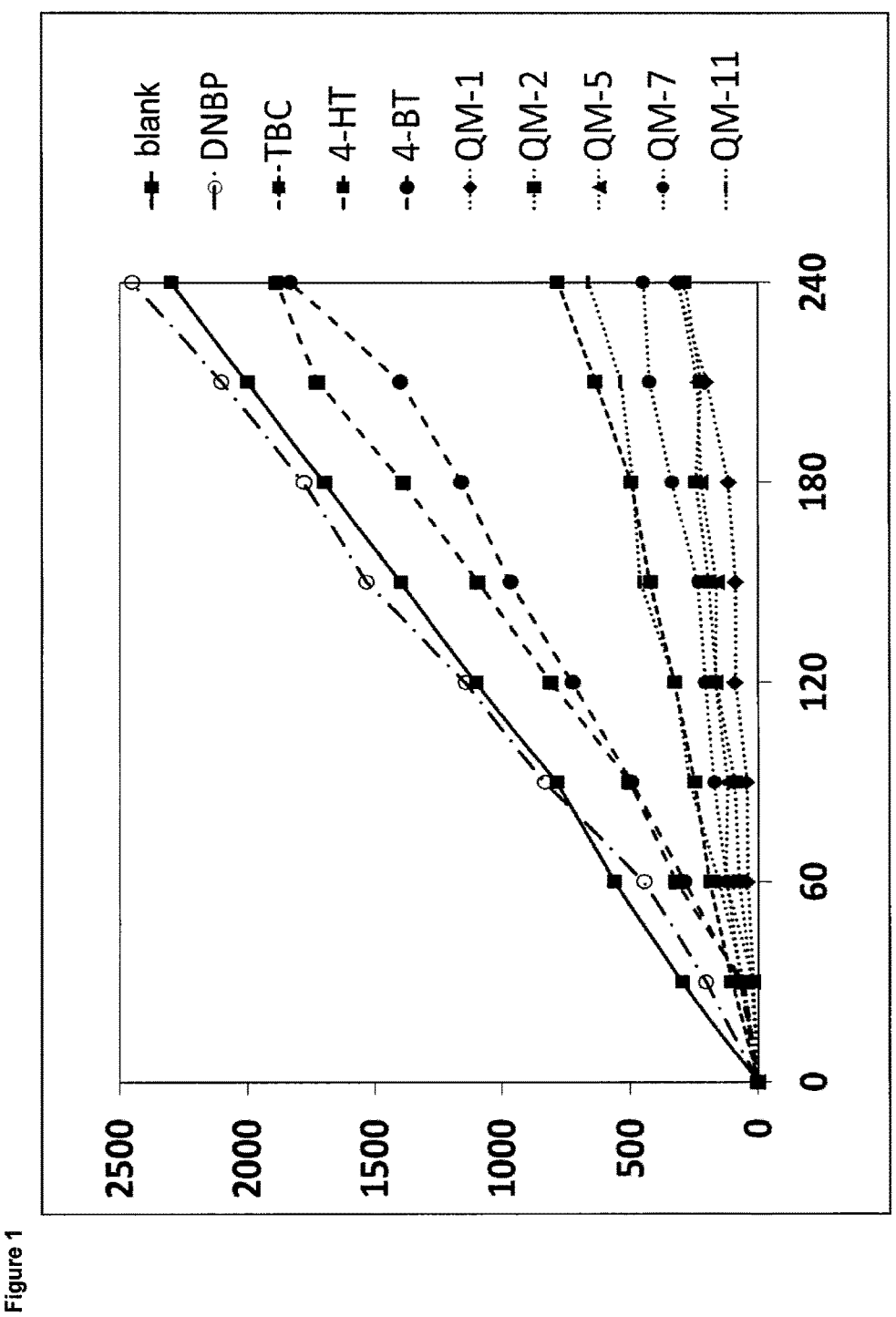
FIG. 1 shows the results obtained in Examples 1 to 11 on comparing certain compounds previously employed and the compounds of the invention in a test of their ability to stabilize pure (di-)cyclopentadiene against polymerization at 170° C. oil bath temperature. The x-axis represents the time in minutes and the y-axis the peak area measured using ELS. Abbreviations: 4-hydroxy-TEMPO (4-HT), 4-butoxy-TEMPO (4-BT), tert-butyl-catechol (TBC) and dinitro-sec-butylphenol (DNBP). The structure of QM-1 is (V), the structure of QM-2 is (VI), the structure of QM-5 is (X), the structure of QM-7 is (XII) and the structure of QM-11 is (XVI).

Exact experimental descriptions are found in the Examples section.

DESCRIPTION OF THE PREFERRED EMBODIMENTS

General Terms

Throughout this description all ranges described include all values and sub-ranges therein, unless otherwise specified.

Additionally, the indefinite article "a" or "an" carries the meaning of "one or more" throughout the description, unless otherwise specified.

The term "cyclopentadiene compound" for the purposes of the present invention describes a compound selected from the group consisting of cyclopentadiene, dicyclopentadiene, alkylated cyclopentadiene and alkylated dicyclopentadiene, preferably selected from the group consisting of cyclopentadiene and dicyclopentadiene.

Cyclopentadiene (CPD) has structure (II).

Dicyclopentadiene (DCPD) has structure (Ill) and possesses two isomeric forms, endo-dicyclopentadiene (endo-DCPD) and exo-dicyclopentadiene (exo-DCPD).

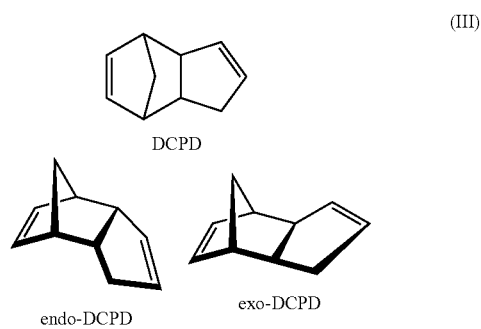

The term "(di)cyclopentadiene" for the purposes of the present invention refers to mixtures of CPD and DCPD.

The expression "polymerization of (B)" describes any polymerization involving (B), preferably an oligomerization/polymerization with itself or vinylic structures.

The term "alkylated cyclopentadiene" for the purposes of the present invention describes compounds of structure (IV).

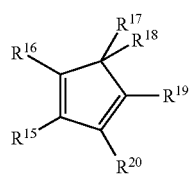

(IV)

where, in the compound of structure (IV), at least one of $R^{15}$, $R^{16}$, $R^{17}$, $R^{18}$, $R^{19}$, $R^{20}$ is alkyl having 1 to 18 carbon atoms while the others are each hydrogen. In one preferred embodiment, "alkylated cyclopentadiene" is monoalkylcyclopentadiene or dialkylcyclopentadiene, more preferably monoalkylcyclopentadiene.

The term "monoalkylcyclopentadiene" for the purposes of the present invention describes the compounds of structure (IV) where precisely one of $R^{15}$, $R^{16}$, $R^{17}$, $R^{18}$, $R^{19}$, $R^{20}$ is alkyl having 1 to 18 carbon atoms, preferably alkyl having 1 to 6 carbon atoms, more preferably methyl or ethyl, most preferably methyl, while the others are each hydrogen.

The term "dialkylcyclopentadiene" for the purposes of the present invention describes the compounds of structure (IV) where precisely two of $R^{15}$, $R^{16}$, $R^{17}$, $R^{18}$, $R^{19}$, $R^{20}$ are each independently alkyl of 1 to 18 carbon atoms, preferably alkyl of 1 to 6 carbon atoms, more preferably methyl or ethyl, most preferably methyl, while the others are each hydrogen.

The term "alkylated dicyclopentadiene" for the purposes of the present invention describes any molecule of structure (III) where at least one hydrogen is replaced by alkyl of 1 to 18 carbon atoms, preferably by alkyl of 1 to 6 carbon atoms, more preferably by methyl or ethyl.

The term "alkylated dicyclopentadiene" for the purposes of the present invention describes in one very particularly preferred embodiment any molecule of structure (111) where precisely one hydrogen, precisely two hydrogens, precisely three hydrogens or precisely four hydrogens is/are replaced by alkyl of 1 to 6 carbon atoms, more preferably by methyl or ethyl.

Alkyl of 1 to 18 carbon atoms has for the purposes of the present invention between 1 and 18 saturated carbon atoms and may be linear or branched and may be more particularly selected from methyl, ethyl, n-propyl, iso-propyl, n-butyl, sec-butyl, iso-butyl, tert-butyl, n-pentyl, 1-methylbutyl, 2-methylbutyl, 3-methylbutyl, 1,1-dimethyl propyl, 1,2-dimethylpropyl, 2,2-dimethylpropyl, 1-ethylpropyl, n-hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, heptyl, octyl, nonyl, decyl, undecyl, dodecyl, tridecyl, tetradecyl, pentadecyl, hexadecyl, heptadecyl, octadecyl. Alkyl of 1 to 12 carbon atoms has for the purposes of the present invention between 1 and 12 saturated carbon atoms and may be linear or branched and may be more particularly selected from methyl, ethyl, n-propyl, iso-propyl, n-butyl, sec-butyl, iso-butyl, tert-butyl, n-pentyl, 1-methylbutyl, 2-methylbutyl, 3-methylbutyl, 1,1-dimethylpropyl, 1,2-dimethylpropyl, 2,2-dimethylpropyl, 1-ethylpropyl, n-hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, heptyl, octyl, nonyl, decyl, undecyl, dodecyl.

Alkyl of 1 to 6 carbon atoms has for the purposes of the present invention between 1 and 6 saturated carbon atoms and may be linear or branched and may be more particularly selected from methyl, ethyl, n-propyl, iso-propyl, n-butyl, sec-butyl, iso-butyl, tert-butyl, n-pentyl, 1-methylbutyl, 2-methylbutyl, 3-methylbutyl, 1,1-dimethylpropyl, 1,2-dimethylpropyl, 2,2-dimethylpropyl, 1-ethylpropyl, n-hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl.

Alkyl of 1 to 4 carbon atoms has for the purposes of the present invention between 1 and 4 saturated carbon atoms and may be linear or branched and may be more particularly selected from methyl, ethyl, n-propyl, iso-propyl, n-butyl, sec-butyl, iso-butyl, tert-butyl.

Alkyl of 1 to 3 carbon atoms has for the purposes of the present invention between 1 and 3 saturated carbon atoms and may be linear or branched and may be more particularly selected from methyl, ethyl, n-propyl, iso-propyl.

Cycloalkyl of 3 to 15 carbon atoms is for the purposes of the present invention more particularly selected from cyclopropyl, cyclobutyl, cyclopropylmethyl, cyclopentyl, cyclobutylmethyl, cyclohexyl, cycloheptyl, cyclooctyl, cyclononyl, cyclodecyl, cycloundecyl, cyclododecyl, cyclotridecyl, cyclotetradecyl, cyclopentadecyl.

Cycloalkyl of 3 to 12 carbon atoms is for the purposes of the present invention more particularly selected from cyclopropyl, cyclobutyl, cyclopropylmethyl, cyclopentyl, cyclobutylmethyl, cyclohexyl, cycloheptyl, cyclooctyl, cyclononyl, cyclodecyl, cycloundecyl, cyclododecyl.

Aryl of 6 to 15 carbon atoms is more particularly selected from phenyl, 1-naphthyl, 2-naphthyl, 9-anthryl, 9-phenanthryl.

Aryl of 6 to 10 carbon atoms is for the purposes of the present invention more particularly selected from phenyl, 1-naphthyl, 2-naphthyl.

Phenylalkyl of 7 to 15 carbon atoms comprises for the purposes of the present invention branched or unbranched alkyl with an attached phenyl ring, and is more particularly selected from benzyl, phenylethyl, α-methylbenzyl, 3-phenylpropyl, phenyl-2-methylethyl, phenyl-1-methylethyl, α,α-dimethylbenzyl, butylphenyl, hexylphenyl, octylphenyl, nonyiphenyl, preferably benzyl.

Alkylamino of 1 to 4 carbon atoms for the purposes of the present invention refers more particularly to an amino moiety comprising an alkyl group of 1 to 4 carbon atoms, and is preferably selected from methylamino, ethylamino, propylamino, isopropylamino and butylamino.

Dialkylamino for the purposes of the present invention is more particularly an amino moiety which bears two alkyl groups, and is more particularly dialkylamino of 2 to 8 carbon atoms.

Dialkylamino of 2 to 8 carbon atoms for the purposes of the present invention refers more particularly to an amino moiety comprising two alkyl groups of 1 to 4 carbon atoms, wherein these alkyl groups of 1 to 4 carbon atoms can be the same or different, and is preferably selected from dimethylamino, diethylamino, dipropylamino, dibutylamino, methylethylamino and methylbutylamino.

"High-boiling hydrocarbon cuts" for the purposes of the present invention denotes aliphatic or aromatic hydrocarbon cuts having fixed boiling ranges, in particular aromatic hydrocarbons having a boiling point (at atmospheric pressure) in the range from 155° C. to 300° C., these preferably contain one or more substances selected from the group consisting of n-propylbenzene, 1-methyl-4-ethylbenzene, 1-methyl-3-ethylbenzene, mesitylene, 1-methyl-2-ethylbenzene, 1,2,4-trimethylbenzene, 1,2,3-trimethylbenzene, indane, 1,3-diethylbenzene, 1-methyl-4-propylbenzene, 1-methyl-3-propylbenzene, 1,2,4,5-tetramethylbenzene, 1,2,3,5-tetramethylbenzene and naphthalene.

Process According to the Invention

The expression "process according to the invention" is synonymous with "process for inhibiting the polymerization of (B)".

The invention provides a process for inhibiting the polymerization of (B), said process being characterized in that (A) and (B) are brought into contact, wherein (A) is at least one compound of structure (I)

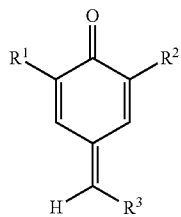

(I)

wherein
$R^1$ and $R^2$ are each independently hydrogen, alkyl of 1 to 18 carbon atoms, cycloalkyl of 3 to 15 carbon atoms, aryl of 6 to 15 carbon atoms or phenylalkyl of 7 to 15 carbon atoms;
$R^3$ is —CN, —COOH, —COOR$^4$, —COR$^5$, —OCOR$^6$, —CONR$^7$R$^8$, —PO(OR$^9$)$_2$, —O—R$^{10}$, —S—R$^{11}$, —R$^{12}$, —C≡C—R$^{13}$ or halogen;
wherein
$R^4$, $R^5$, $R^6$ is alkyl of 1 to 18 carbon atoms, cycloalkyl of 3 to 12 carbon atoms, aryl of 6 to 10 carbon atoms;
$R^7$ and $R^8$ are each independently hydrogen; alkyl of 1 to 15 carbon atoms which is unsubstituted or substituted with at least one substituent selected from the group consisting of alkylamino having 1 to 4 carbon atoms, dialkylamino having 2 to 8 carbon atoms and hydroxyl; phenylalkyl of 7 to 15 carbon atoms which is unsubstituted or substituted with at least one substituent selected from the group consisting of hydroxyl, alkyl having 1 to 4 carbon atoms, alkylamino having 1 to 4 carbon atoms and dialkylamino having 2 to 8 carbon atoms; aryl of 6 to 10 carbon atoms which is unsubstituted or substituted with at least one substituent selected from the group consisting of alkyl having 1 to 4 carbon atoms, alkylamino having 1 to 4 carbon atoms, dialkylamino having 2 to 8 carbon atoms and hydroxyl; or NR$^7$R$^8$ is morpholino, piperidino or pyrrolidino;
$R^9$, $R^{10}$, $R^{11}$ are hydrogen; alkyl of 1 to 15 carbon atoms which is unsubstituted or substituted with at least one substituent selected from the group consisting of hydroxyl, dialkylamino, —OR$^{14}$, —[O(CH$_2$)$_y$]$_x$H, where x is 1, 2, 3, 4, 5, 6, 7, 8, 9 or 10 and y is 1, 2, 3 or 4 and where R$^{14}$ is alkyl of 1 to 6 carbon atoms; cycloalkyl of 3 to 15 carbon atoms which is unsubstituted or substituted with at least one substituent selected from the group consisting of hydroxyl, dialkylamino, —OR$^{14}$, —[O(CH$_2$)$_y$]$_x$H, where x is 1, 2, 3, 4, 5, 6, 7, 8, 9 or 10 and y is 1, 2, 3 or 4 and where R$^{14}$ is alkyl of 1 to 6 carbon atoms; phenylalkyl of 7 to 15 carbon atoms which is unsubstituted or substituted with at least one substituent selected from the group consisting of hydroxyl, dialkylamino, —OR$^{14}$, —[O(CH$_2$)$_y$]$_x$H, where x is 1, 2, 3, 4, 5, 6, 7, 8, 9 or 10 and y is 1, 2, 3 or 4 and where R$^{14}$ is alkyl of 1 to 6 carbon atoms; or aryl of 6 to 15 carbon atoms which is unsubstituted or substituted with at least one substituent selected from the group consisting of hydroxyl, dialkylamino, —OR$^{14}$, —[O(CH$_2$)$_y$]$_x$H, where x is 1, 2, 3, 4, 5, 6, 7, 8, 9 or 10 and y is 1, 2, 3 or 4 and where R$^{14}$ is alkyl of 1 to 6 carbon atoms;
$R^{12}$ is 2-pyridyl, 3-pyridyl, 4-pyridyl, 2-thienyl, 3-thienyl, 2-pyrryl, 3-pyrryl, 2-furyl, 3-furyl or aryl of 6 to 15 carbon atoms; wherein the radicals 2-pyridyl, 3-pyridyl, 4-pyridyl, 2-thienyl, 3-thienyl, 2-pyrryl, 3-pyrryl, 2-furyl, 3-furyl or aryl of 6 to 15 carbon atoms are unsubstituted or substituted with at least one substituent selected from the group consisting of hydroxyl, nitro, amino, cyano, carboxyl, aminocarbonyl, halogen, alkyl of 1 to 8 carbon atoms, alkoxy of 1 to 8 carbon atoms, alkylthio of 1 to 8 carbon atoms, alkylamino of 1 to 8 carbon atoms, dialkylamino of 2 to 8 carbon atoms and a carboxylic ester group of 2 to 8 carbon atoms;
$R^{13}$ is hydrogen, alkyl of 1 to 12 carbon atoms, aryl of 6 to 10 carbon atoms, wherein the aryl of 6 to 10 carbon atoms is unsubstituted or substituted with at least one substituent selected from the group consisting of hydroxyl, nitro, amino, cyano, carboxyl, aminocarbonyl, halogen, alkyl of 1 to 8 carbon atoms, alkoxy of 1 to 8 carbon atoms, alkylthio of 1 to 8 carbon atoms, alkylamino of 1 to 8 carbon atoms, dialkylamino of 2 to 8 carbon atoms and a carboxylic ester group of 2 to 8 carbon atoms;
wherein the substituents $R^1$, $R^2$ and $R^3$ are the same or different; and
(B) is at least one cyclopentadiene compound.

In one preferred embodiment of the process according to the invention, $R^1$ and $R^2$ in the compound of structure (I) are each independently selected from the group consisting of methyl, ethyl, n-propyl, iso-propyl, n-butyl, iso-butyl and tert-butyl; and
$R^3$=—CN, —COOH, —COOR$^4$, —COR$^5$, —OCOR$^6$, —CONR$^7$R$^8$, —PO(OR$^9$)$_2$, —O—R$^{10}$, —S—R$^{11}$, —R$^{12}$—C≡C—R$^{13}$ or halogen; wherein R$^4$, R$^5$, R$^6$ are alkyl of 1 to 8 carbon atoms or phenyl;
$R^7$R$^8$ are each independently hydrogen or alkyl of 1 to 4 carbon atoms, or NR$^7$R$^8$ is morpholino or piperidino;
$R^9$, $R^{10}$, $R^{11}$ are alkyl of 1 to 8 carbon atoms or phenyl;

R¹² is 2-furyl, 3-furyl or aryl of 6 to 15 carbon atoms, wherein the radicals 2-furyl, 3-furyl or aryl of 6 to 15 carbon atoms are unsubstituted or substituted with at least one substituent selected from the group consisting of hydroxyl and alkyl of 1 to 8 carbon atoms;

R¹³ is hydrogen, alkyl of 1 to 12 carbon atoms, aryl of 6 to 10 carbon atoms.

In one more preferred embodiment of the process according to the invention, $R^1$ and $R^2$ are each independently selected from the group consisting of methyl and tert-butyl in the compound of structure (I); and $R^3$ is —CN, —COOH, —COOR⁴, —S—R¹¹, —R¹², —C≡C—R¹³ or halogen; wherein R⁴ is alkyl of 1 to 4 carbon atoms;

R¹⁰, R¹¹ are alkyl of 1 to 6 carbon atoms;

R¹² is 2-furyl, 3-furyl or aryl of 6 to 12 carbon atoms, wherein the radicals 2-furyl, 3-furyl or aryl of 6 to 12 carbon atoms are unsubstituted or substituted with at least one substituent selected from the group consisting of hydroxyl and alkyl of 1 to 8 carbon atoms;

R¹³ is aryl of 6 to 10 carbon atoms.

In one still more preferred embodiment of the process according to the invention $R^1$ and $R^2$ are each tert-butyl in the compound of structure (I); and $R^3$ is —CN, —COOH, —O—R¹⁰, —S—R¹¹, —R¹² or —C≡C—R¹³;

wherein

R¹⁰ is methyl, ethyl, iso-propyl, n-propyl, n-butyl, iso-butyl, sec-butyl, tert-butyl, n-pentyl, 1-methylbutyl, 2-methylbutyl, 3-methylbutyl, 1,1-dimethylpropyl, 1,2-dimethylpropyl, 2,2-dimethylpropyl, 1-ethylpropyl, n-hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl or 1-ethyl-2-methylpropyl, preferably methyl, ethyl, iso-propyl, n-propyl, sec-butyl, n-butyl, n-pentyl, or n-hexyl;

R¹¹ is alkyl of 1 to 6 carbon atoms;

R¹² is 2-furyl, 3-furyl or phenyl, wherein phenyl is unsubstituted or substituted with at least one substituent selected from the group consisting of hydroxyl and alkyl of 1 to 8 carbon atoms;

R¹³ is phenyl.

In a first very particularly preferred embodiment of the process according to the invention, the compound of structure (I) has $R^1$ and $R^2$ being tert-butyl and $R^3$ is CN, the compound of structure (I) then having structure (V) (hereinafter also abbreviated as "QM-1")

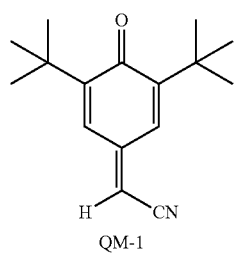

QM-1 and the cyclopentadiene compound is selected from the group consisting of cyclopentadiene, dicyclopentadiene, alkylated cyclopentadiene and alkylated dicyclopentadiene, more preferably selected from the group consisting of cyclopentadiene and dicyclopentadiene.

In a second very particularly preferred embodiment of the process according to the invention, the compound of structure (I) has $R^1$ and $R^2$ being tert-butyl and $R^3$ is phenyl, the compound of structure (I) then having structure (VI) (hereinafter also abbreviated as "QM-2")

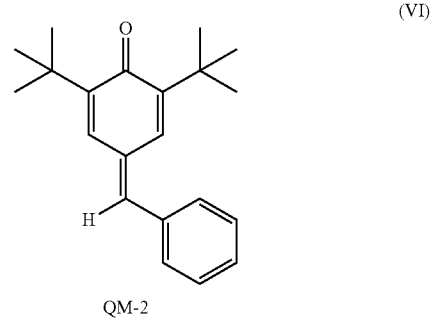

QM-2 and the cyclopentadiene compound is selected from the group consisting of cyclopentadiene, dicyclopentadiene, alkylated cyclopentadiene and alkylated dicyclopentadiene, more preferably selected from the group consisting of cyclopentadiene and dicyclopentadiene.

In a third very particularly preferred embodiment of the process according to the invention, the compound of structure (I) has $R^1$ and $R^2$ being tert-butyl and $R^3$ is 3,5-di-tert-butyl-4-hydroxyphenyl, the compound of structure (I) then having structure (VII) (hereinafter also abbreviated as "QM-3")

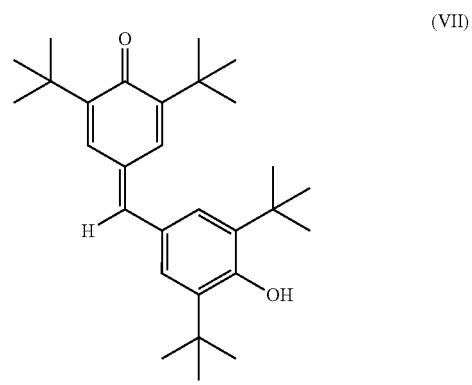

QM-3 and the cyclopentadiene compound is selected from the group consisting of cyclopentadiene, dicyclopentadiene, alkylated cyclopentadiene and alkylated dicyclopentadiene, more preferably selected from the group consisting of cyclopentadiene and dicyclopentadiene.

In a fourth very particularly preferred embodiment of the process according to the invention, the compound of structure (I) has $R^1$ and $R^2$ being tert-butyl and $R^3$ is 2-furyl, the compound of structure (I) then having structure (VIII) (hereinafter also abbreviated as "QM-4")

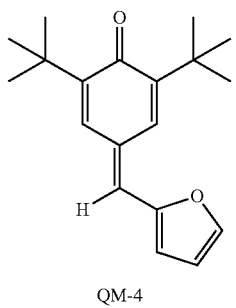

(VIII)

QM-4 and the cyclopentadiene compound is selected from the group consisting of cyclopentadiene, dicyclopentadiene, alkylated cyclopentadiene and alkylated dicyclopentadiene, more preferably selected from the group consisting of cyclopentadiene and dicyclopentadiene.

In a fifth very particularly preferred embodiment of the process according to the invention, the compound of structure (I) has $R^1$ and $R^2$ being tert-butyl and $R^3$ is —$OR^{10}$, wherein $R^{10}$ is methyl, ethyl, iso-propyl, n-propyl, n-butyl, sec-butyl, iso-butyl, tert-butyl, n-pentyl, 1-methylbutyl, 2-methylbutyl, 3-methylbutyl, 1,1-dimethylpropyl, 1,2-dimethylpropyl, 2,2-dimethylpropyl, 1-ethylpropyl, n-hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl or 1-ethyl-2-methylpropyl, preferably methyl, ethyl, iso-propyl, n-propyl, n-butyl, sec-butyl, tert-butyl, n-pentyl or n-hexyl, more preferably methyl, ethyl, n-propyl, iso-propyl, n-butyl, n-pentyl or n-hexyl; the compound of structure (I) then having structure (IX)

(IX)

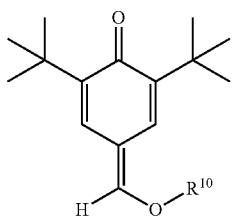

and the cyclopentadiene compound is selected from the group consisting of cyclopentadiene, dicyclopentadiene, alkylated cyclopentadiene and alkylated dicyclopentadiene, more preferably selected from the group consisting of cyclopentadiene and dicyclopentadiene.

In a sixth very particularly preferred embodiment of the process according to the invention, the compound of structure (I) has $R^1$ and $R^2$ being tert-butyl and $R^3$ is —$OCH_3$, the compound of structure (I) then having structure (X) (hereinafter also abbreviated as "QM-5")

(X)

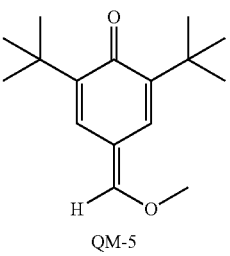

QM-5 and the cyclopentadiene compound is selected from the group consisting of cyclopentadiene, dicyclopentadiene, alkylated cyclopentadiene and alkylated dicyclopentadiene, more preferably selected from the group consisting of cyclopentadiene and dicyclopentadiene.

In a seventh very particularly preferred embodiment of the process according to the invention, the compound of structure (I) has $R^1$ and $R^2$ being tert-butyl and $R^3$ is —$OCH_2CH_3$, the compound of structure (I) then having structure (XI) (hereinafter also abbreviated as "QM-6")

(XI)

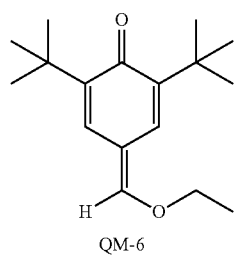

QM-6 and the cyclopentadiene compound is selected from the group consisting of cyclopentadiene, dicyclopentadiene, alkylated cyclopentadiene and alkylated dicyclopentadiene, more preferably selected from the group consisting of cyclopentadiene and dicyclopentadiene.

In an eighth very particularly preferred embodiment of the process according to the invention, the compound of structure (I) has $R^1$ and $R^2$ being tert-butyl and $R^3$ is —$OCH_2CH_2CH_3$, the compound of structure (I) then having structure (XII) (hereinafter also abbreviated as "QM-7")

(XII)

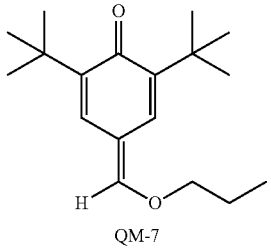

QM-7 and the cyclopentadiene compound is selected from the group consisting of cyclopentadiene, dicyclopentadiene, alkylated cyclopentadiene and alkylated dicyclopentadiene, more preferably selected from the group consisting of cyclopentadiene and dicyclopentadiene.

In a ninth very particularly preferred embodiment of the process according to the invention, the compound of structure (I) has $R^1$ and $R^2$ being tert-butyl and $R^3$ is —OCH$(CH_3)_2$, the compound of structure (I) then having structure (XIII) (hereinafter also abbreviated as "QM-8."

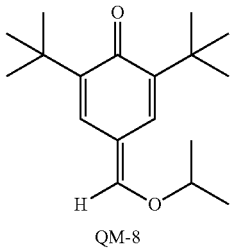

QM-8

(XIII)

and the cyclopentadiene compound is selected from the group consisting of cyclopentadiene, dicyclopentadiene, alkylated cyclopentadiene and alkylated dicyclopentadiene, more preferably selected from the group consisting of cyclopentadiene and dicyclopentadiene.

In a tenth very particularly preferred embodiment of the process according to the invention, the compound of structure (I) has $R^1$ and $R^2$ being tert-butyl and $R^3$ is —OCH$_2$CH$_2$CH$_2$CH$_3$, the compound of structure (I) then having structure (XIV) (hereinafter also abbreviated as "QM-9")

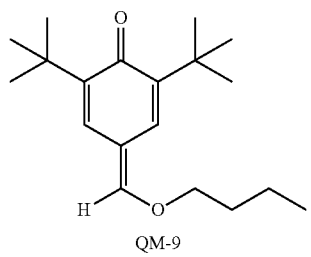

QM-9

(XIV)

and the cyclopentadiene compound is selected from the group consisting of cyclopentadiene, dicyclopentadiene, alkylated cyclopentadiene and alkylated dicyclopentadiene, more preferably selected from the group consisting of cyclopentadiene and dicyclopentadiene.

In an eleventh very particularly preferred embodiment of the process according to the invention, the compound of structure (I) has $R^1$ and $R^2$ being tert-butyl and $R^3$ is —OCH$_2$CH$_2$CH$_2$CH$_2$CH$_3$, the compound of structure (I) then having structure (XV) (hereinafter also abbreviated as "QM-10")

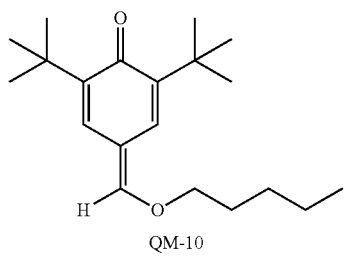

QM-10

(XV)

and the cyclopentadiene compound is selected from the group consisting of cyclopentadiene, dicyclopentadiene, alkylated cyclopentadiene and alkylated dicyclopentadiene, more preferably selected from the group consisting of cyclopentadiene and dicyclopentadiene.

In a twelfth very particularly preferred embodiment of the process according to the invention, the compound of structure (I) has $R^1$ and $R^2$ being tert-butyl and $R^3$ is —OCH$_2$CH$_2$CH$_2$CH$_2$CH$_2$CH$_3$, the compound of structure (I) then having structure (XVI) (hereinafter abbreviated as "QM-11")

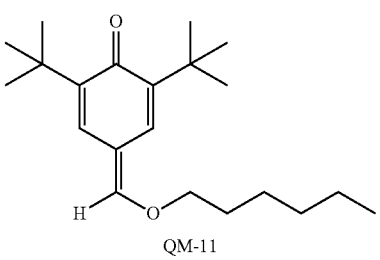

QM-11

(XVI)

and the cyclopentadiene compound is selected from the group consisting of cyclopentadiene, dicyclopentadiene, alkylated cyclopentadiene and alkylated dicyclopentadiene, more preferably selected from the group consisting of cyclopentadiene and dicyclopentadiene.

In a thirteenth very particularly preferred embodiment of the process according to the invention, the compound of structure (I) has $R^1$ and $R^2$ being tert-butyl and $R^3$ is —C≡C-phenyl, the compound of structure (I) then having structure (XVII) (hereinafter abbreviated as "QM-12")

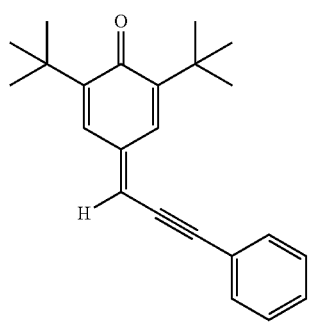

QM-12

(XVII)

and the cyclopentadiene compound is selected from the group consisting of cyclopentadiene, dicyclopentadiene, alkylated cyclopentadiene and alkylated dicyclopentadiene, more preferably selected from the group consisting of cyclopentadiene and dicyclopentadiene.

In a fourteenth very particularly preferred embodiment of the process according to the invention, the compound of structure (I) has $R^1$ and $R^2$ being tert-butyl and $R^3$ is —COOH, the compound of structure (I) then having structure (XVIII) (hereinafter abbreviated as "QM-13")

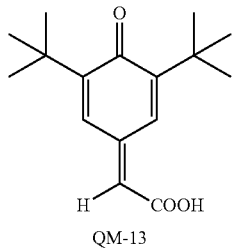

(XVIII)

QM-13 and the cyclopentadiene compound is selected from the group consisting of cyclopentadiene, dicyclopentadiene, alkylated cyclopentadiene and alkylated dicyclopentadiene, more preferably selected from the group consisting of cyclopentadiene and dicyclopentadiene.

In a fifteenth very particularly preferred embodiment of the process according to the invention, the compound of structure (I) has $R^1$ and $R^2$ being tert-butyl and $R^3$ is —$SCH_2CH_2CH_2CH_3$, the compound of structure (I) then having structure (XIX) (hereinafter abbreviated as "QM-14")

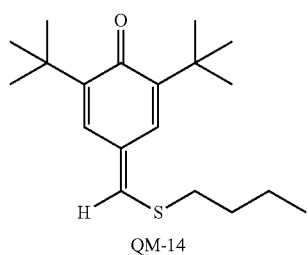

(XIX)

QM-14 and the cyclopentadiene compound is selected from the group consisting of cyclopentadiene, dicyclopentadiene, alkylated cyclopentadiene and alkylated dicyclopentadiene, more preferably selected from the group consisting of cyclopentadiene and dicyclopentadiene.

(A) may be used in the process according to the invention in gaseous form, as a solid material (as a powder, for example) or as a liquid, in particular as a solid material (as a powder, for example) or as a liquid, preferably as a liquid. (A) used as a liquid in the process according to the invention is more particularly used as a melt or in the form of a solution in (C), where "(C)" has the meaning "at least one solvent".

Any material may be useful as a solvent in the process according to the invention provided (A) is soluble therein in the desired concentration range and it is both compatible with (A) and does not have a disruptive effect on the process according to the invention, and may be an apolar solvent, preferably an apolar aromatic or aliphatic solvent. It may be more preferable for the solvent in the process according to the invention to be selected from the group consisting of benzene, mono- or polyalkylated aromatics, alkanes having a carbon number of 6 to 15, cycloalkanes having a carbon number of 6 to 15, high-boiling hydrocarbon cuts, ethers having a carbon number of 6 to 15 and esters having a carbon number of 6 to 15. It may be still more preferable for the solvent in the process according to the invention to be selected from the group consisting of benzene, toluene, ethylbenzene, xylene, styrene and high-boiling aromatic hydrocarbon cuts. It may be particularly preferable for the solvent in the process according to the invention to be selected from the group consisting of toluene, ethylbenzene, xylene and styrene. Alternatively, the cyclopentadiene compound itself can also serve as the solvent in the process according to the invention.

When (A) is used in the process according to the invention in the form of a solution in (C), the total weight of all compounds of structure (I) in said solution (AC) preferably has an (m/m) ratio to the total weight of all solvents in said solution (AC) in the range from 1:1000 to 100:1, more preferably in the range from 1:100 to 10:1 and still more preferably in the range from 1:10 to 3:1.

(B) may be present in the process according to the invention in gaseous form, as a liquid or as a solid material, in particular in gaseous form or as a liquid, preferably as a liquid. (B) as a liquid is still more preferably in the form of a melt or solution. It may be particularly preferable for (B) to be in the form of a solution. Such a solution in a first very particularly preferred embodiment is a process stream as obtained in cracking processes. (B) may typically be present in such a process stream at from 0.0001 wt % to 15 wt %.

In an alternative second very particularly preferred embodiment, the solution may be a process stream as generated in the production of DCPD and/or CPD itself. (B) is typically present in such a process stream at between 15 and 100 wt %, preferably between 70 and 100 wt % and still more preferably between 70 and 99.99 wt %.

The expression "bringing (A) and (B) into contact" for the purposes of the invention is to be understood as meaning in particular that (A) is admixed to (B) or (B) is admixed to (A). Admixing (A) to (B) or (B) to (A) can be effected according to conventionally known methods.

(A) may be admixed with advantage in the process according to the invention into any feedstream or outflow line of a distillation column, into the in- and outflow line of a heat exchanger or into the in- and outflow line of a vaporizer ("reboiler") or into the in- and outflow line of a condenser or into the in- and outflow line of a reactor. (A) may also be added in the process according to the invention to storage tanks containing a process stream comprising (B). (A) may be admixed to (B) not only before but also during a process, for example a production or purification process.

An effective amount of (A) is admixed in the process according to the invention. The term "effective amount of (A)" in the context of this invention may be understood as meaning the amount of (A) needed to delay/prevent the undesired polymerization of (B). This effective amount depends on the conditions under which the cyclopentadiene compound, or mixture of two or more cyclopentadiene compounds, is stored or handled and can readily be determined from case to case by a person skilled in the art. For example, the cracking of dicyclopentadiene requires by reason of the higher temperatures a higher amount of (A) than the storing of (B) at for instance room temperature.

(A) may preferably be used in the process according to the invention in such an amount that the total concentration of all compounds of structure (I) is between 10 ppb on a mass to mass basis (m/m) and 100,000 ppm (m/m), more preferably between 1 ppm (m/m) and 50,000 ppm (m/m), even more preferably between 10 ppm and 10,000 ppm (m/m), most preferably between 100 ppm and 5000 ppm (m/m), each based on the total weight of all cyclopentadiene compounds.

The temperature at which the process according to the invention may be carried out is not subject to any in-principle limitation; on the contrary, it is a feature of the present invention that the process according to the invention can be carried out not only at low but also at high temperatures, in particular in the range from 0° C. to 250° C., preferably 0° C. to 200° C.

The process according to the invention may utilize a polymerization inhibitor (D) as well as (A). Polymerization inhibitors of this type are conventionally known, examples being nitroxides such as, for instance, oxo-TEMPO or 4-hydroxy-TEMPO, phenylenediamines, hydroxylamines such as diethylhydroxylamine (DEHA), nitro- or nitrosoaromatics such as DNBP, (di)phenols such as hydroquinone, TBC or 2,6-di-tert-butylphenol, benzoquinones, phenothiazines such as PTZ.

Composition According to the Invention

The invention also provides a composition (AB), comprising (A) and (B),
wherein
(A) is at least one compound of structure (I)

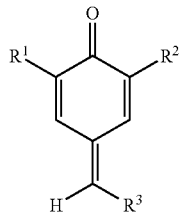

(I)

wherein
$R^1$ and $R^2$ are each independently hydrogen, alkyl of 1 to 18 carbon atoms, cycloalkyl of 3 to 15 carbon atoms, aryl of 6 to 15 carbon atoms or phenylalkyl of 7 to 15 carbon atoms;
$R^3$ is —CN, —COOH, —COOR$^4$, —COR$^5$, —OCOR$^6$, —CONR$^7$R$^8$, —PO(OR$^9$)$_2$, —O—R$^{10}$, —S—R$^{11}$, —R$^{12}$, —C≡C—R$^{13}$ or halogen;
wherein
$R^4$, $R^5$, $R^6$ are alkyl of 1 to 18 carbon atoms, cycloalkyl of 3 to 12 carbon atoms, aryl of 6 to 10 carbon atoms;
$R^7$ and $R^8$ are each independently hydrogen; alkyl of 1 to 15 carbon atoms which is unsubstituted or substituted with at least one substituent selected from the group consisting of alkylamino having 1 to 4 carbon atoms, dialkylamino having 2 to 8 carbon atoms and hydroxyl; phenylalkyl of 7 to 15 carbon atoms which is unsubstituted or substituted with at least one substituent selected from the group consisting of hydroxyl, alkyl having 1 to 4 carbon atoms, alkylamino having 1 to 4 carbon atoms and dialkylamino having 2 to 8 carbon atoms; aryl of 6 to 10 carbon atoms which is unsubstituted or substituted with at least one substituent selected from the group consisting of alkyl having 1 to 4 carbon atoms, alkylamino having 1 to 4 carbon atoms, dialkylamino having 2 to 8 carbon atoms and hydroxyl; or NR$^7$R$^8$ is morpholino, piperidino or pyrrolidino;
$R^9$, $R^{10}$, $R^{11}$ are hydrogen; alkyl of 1 to 15 carbon atoms which is unsubstituted or substituted with at least one substituent selected from the group consisting of hydroxyl, dialkylamino, —OR$^{14}$, —[O(CH$_2$)$_y$]$_x$H, where x is 1, 2, 3, 4, 5, 6, 7, 8, 9 or 10 and y is 1, 2, 3 or 4 and where R$^{14}$ is alkyl of 1 to 6 carbon atoms; cycloalkyl of 3 to 15 carbon atoms which is unsubstituted or substituted with at least one substituent selected from the group consisting of hydroxyl, dialkylamino, —OR$^{14}$, —[O(CH$_2$)$_y$]$_x$H, where x is 1, 2, 3, 4, 5, 6, 7, 8, 9 or 10 and y is 1, 2, 3 or 4 and where R$^{14}$ is alkyl of 1 to 6 carbon atoms; phenylalkyl of 7 to 15 carbon atoms which is unsubstituted or substituted with at least one substituent selected from the group consisting of hydroxyl, dialkylamino, —OR$^{14}$, —[O(CH$_2$)$_y$]$_x$H, where x is 1, 2, 3, 4, 5, 6, 7, 8, 9 or 10 and y is 1, 2, 3 or 4 and where R$^{14}$ is alkyl of 1 to 6 carbon atoms; or aryl of 6 to 15 carbon atoms which is unsubstituted or substituted with at least one substituent selected from the group consisting of hydroxyl, dialkylamino, —OR$^{14}$, —[O(CH$_2$)$_y$]$_x$H, where x is 1, 2, 3, 4, 5, 6, 7, 8, 9 or 10 and y is 1, 2, 3 or 4 and where R$^{14}$ is alkyl of 1 to 6 carbon atoms; R$^{12}$ is 2-pyridyl, 3-pyridyl, 4-pyridyl, 2-thienyl, 3-thienyl, 2-pyrryl, 3-pyrryl, 2-furyl, 3-furyl or aryl of 6 to 15 carbon atoms; wherein the radicals 2-pyridyl, 3-pyridyl, 4-pyridyl, 2-thienyl, 3-thienyl, 2-pyrryl, 3-pyrryl, 2-furyl, 3-furyl or aryl of 6 to 15 carbon atoms are unsubstituted or substituted with at least one substituent selected from the group consisting of hydroxyl, nitro, amino, cyano, carboxyl, aminocarbonyl, halogen, alkyl of 1 to 8 carbon atoms, alkoxy of 1 to 8 carbon atoms, alkylthio of 1 to 8 carbon atoms, alkylamino of 1 to 8 carbon atoms, dialkylamino of 2 to 8 carbon atoms and a carboxylic ester group of 2 to 8 carbon atoms;
$R^{13}$ is hydrogen, alkyl of 1 to 12 carbon atoms, aryl of 6 to 10 carbon atoms, wherein the aryl of 6 to 10 carbon atoms is unsubstituted or substituted with at least one substituent selected from the group consisting of hydroxyl, nitro, amino, cyano, carboxyl, aminocarbonyl, halogen, alkyl of 1 to 8 carbon atoms, alkoxy of 1 to 8 carbon atoms, alkylthio of 1 to 8 carbon atoms, alkylamino of 1 to 8 carbon atoms, dialkylamino of 2 to 8 carbon atoms and a carboxylic ester group of 2 to 8 carbon atoms;
wherein the substituents $R^1$, $R^2$ and $R^3$ are the same or different, and
(B) is at least one cyclopentadiene compound.

In one preferred embodiment of the composition (AB) according to the invention, $R^1$ and $R^2$ in the compound of structure (I) are each independently selected from the group consisting of methyl, ethyl, n-propyl, iso-propyl, n-butyl, iso-butyl and tert-butyl; and $R^3$ is —CN, —COOH, —COOR$^4$, —COR$^5$, —OCOR$^6$, —CONR$^7$R$^8$, —PO(OR$^9$)$_2$, —O—R$^{10}$, —S—R$^{11}$, —R$^{12}$—C≡C—R$^{13}$ or halogen;
wherein
$R^4$, $R^5$, $R^6$ are alkyl of 1 to 8 carbon atoms or phenyl;
$R^7R^8$ are each independently hydrogen or alkyl of 1 to 4 carbon atoms, or NR$^7$R$^8$ is morpholino or piperidino;
$R^9$, $R^{10}$, $R^{11}$ are alkyl of 1 to 8 carbon atoms or phenyl;
$R^{12}$ is 2-furyl, 3-fury) or aryl of 6 to 15 carbon atoms, wherein the radicals 2-furyl, 3-furyl or aryl of 6 to 15 carbon atoms are unsubstituted or substituted with at least one substituent selected from the group consisting of hydroxyl and alkyl of 1 to 8 carbon atoms; and
$R^{13}$ is hydrogen, alkyl of 1 to 12 carbon atoms, aryl of 6 to 10 carbon atoms.

In one more preferred embodiment of the composition (AB) according to the invention, $R^1$ and $R^2$ in the compound of structure (I) are each independently selected from the group consisting of methyl and tert-butyl; and
$R^3$ is —CN, —COOH, —COOR$^4$, —O—R$^{10}$, —S—R$^{11}$, —R$^{12}$, —C≡C—R$^{13}$ or halogen;

wherein

R⁴ is alkyl of 1 to 4 carbon atoms;

R¹⁰, R¹¹ are alkyl of 1 to 6 carbon atoms;

R¹² is 2-furyl, 3-furyl or aryl of 6 to 12 carbon atoms, wherein the radicals 2-fu 3-furyl or aryl of 6 to 12 carbon atoms are unsubstituted or substituted with at least one substituent selected from the group consisting of hydroxyl and alkyl of 1 to 8 carbon atoms;

R¹³ is aryl of 6 to 10 carbon atoms.

In one still more preferred embodiment of the composition (AB) according to the invention, R¹ and R² are each tert-butyl in the compound of structure (I); and R³ is —CN, —COOH, —O—R¹⁰, s-R¹¹, —R¹² or —C≡C—R¹³;

wherein

R¹⁰ is methyl, ethyl, iso-propyl, n-propyl, n-butyl, iso-butyl, sec-butyl, tert-butyl, n-pentyl, 1-methylbutyl, 2-methylbutyl, 3-methylbutyl, 1,1-dimethylpropyl, 1,2-dimethylpropyl, 2,2-dimethylpropyl, 1-ethylpropyl, n-hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl or 1-ethyl-2-methylpropyl, preferably methyl, ethyl, iso-propyl, n-propyl, sec-butyl, n-butyl, n-pentyl or n-hexyl;

R¹¹ is alkyl of 1 to 6 carbon atoms;

R¹² is 2-furyl, 3-furyl or phenyl, wherein phenyl is unsubstituted or substituted with at least one substituent selected from the group consisting of hydroxyl and alkyl of 1 to 8 carbon atoms; and R¹³ is phenyl.

In a first very particularly preferred embodiment of the composition (AB) according to the invention, the compound of structure (I) has R¹ and R² being tert-butyl and R³ is CN, the compound of structure (I) then having structure (V) (hereinafter also abbreviated as "QM-1")

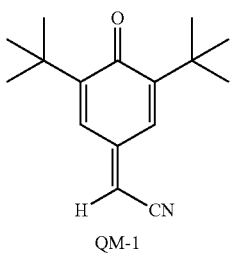

QM-1

(V)

and the cyclopentadiene compound is selected from the group consisting of cyclopentadiene, dicyclopentadiene, alkylated cyclopentadiene and alkylated dicyclopentadiene, more preferably selected from the group consisting of cyclopentadiene and dicyclopentadiene.

In a second very particularly preferred embodiment of the composition (AB) according to the invention, the compound of structure (I) has R¹ and R² being tert-butyl and R³ is phenyl, the compound of structure (I) then having structure (VI) (hereinafter also abbreviated as "QM-2")

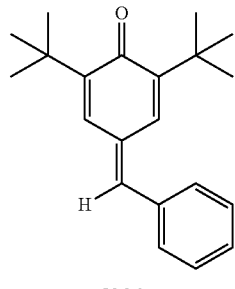

QM-2

(VI)

and the cyclopentadiene compound is selected from the group consisting of cyclopentadiene, dicyclopentadiene, alkylated cyclopentadiene and alkylated dicyclopentadiene, more preferably selected from the group consisting of cyclopentadiene and dicyclopentadiene.

In a third very particularly preferred embodiment of the composition (AB) according to the invention, the compound of structure (I) has R¹ and R² being tert-butyl and R³ is 3,5-di-tert-butyl-4-hydroxyphenyl, the compound of structure (I) then having structure (VII) (hereinafter also abbreviated as "QM-3")

QM-3

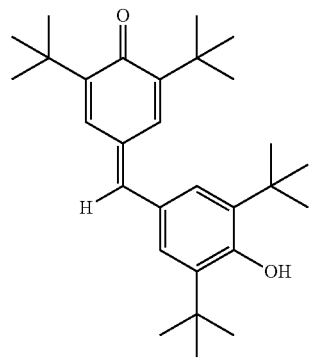

(VII)

and the cyclopentadiene compound is selected from the group consisting of cyclopentadiene, dicyclopentadiene, alkylated cyclopentadiene and alkylated dicyclopentadiene, more preferably selected from the group consisting of cyclopentadiene and dicyclopentadiene.

In a fourth very particularly preferred embodiment of the composition (AB) according to the invention, the compound of structure (I) has R¹ and R² being tert-butyl and R³ is 2-fu the compound of structure (I) then having structure (VIII) (hereinafter also abbreviated as "QM-4")

QM-4

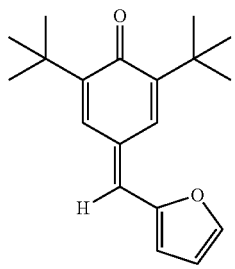

(VIII)

and the cyclopentadiene compound is selected from the group consisting of cyclopentadiene, dicyclopentadiene, alkylated cyclopentadiene and alkylated dicyclopentadiene, more preferably selected from the group consisting of cyclopentadiene and dicyclopentadiene.

In a fifth very particularly preferred embodiment of the composition (AB) according to the invention, the compound of structure (I) has $R^1$ and $R^2$ being tert-butyl and $R^3$ is —$OR^{10}$, wherein $R^{10}$ is methyl, ethyl, iso-propyl, n-propyl, n-butyl, sec-butyl, iso-butyl, tert-butyl, n-pentyl, 1-methylbutyl, 2-methylbutyl, 3-methylbutyl, 1,1-dimethylpropyl, 1,2-dimethylpropyl, 2,2-dimethylpropyl, 1-ethylpropyl, n-hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl or 1-ethyl-2-methylpropyl, preferably methyl, ethyl, iso-propyl, n-propyl, n-butyl, sec-butyl, tert-butyl, n-pentyl or n-hexyl, more preferably methyl, ethyl, n-propyl, iso-propyl, n-butyl, n-pentyl or n-hexyl;

the compound of structure (I) then having structure (IX)

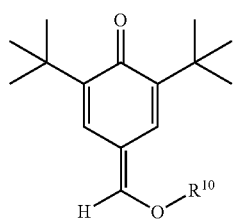

(IX)

and the cyclopentadiene compound is selected from the group consisting of cyclopentadiene, dicyclopentadiene, alkylated cyclopentadiene and alkylated dicyclopentadiene, more preferably selected from the group consisting of cyclopentadiene and dicyclopentadiene.

In a sixth very particularly preferred embodiment of the composition (AB) according to the invention, the compound of structure (I) has $R^1$ and $R^2$ being tert-butyl and $R^3$ is —$OCH_3$, the compound of structure (I) then having structure (X) (hereinafter also abbreviated as "QM-5")

QM-5

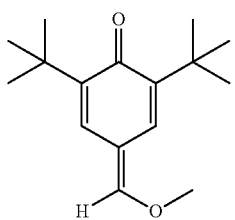

(X)

and the cyclopentadiene compound is selected from the group consisting of cyclopentadiene, dicyclopentadiene, alkylated cyclopentadiene and alkylated dicyclopentadiene, more preferably selected from the group consisting of cyclopentadiene and dicyclopentadiene.

In a seventh very particularly preferred embodiment of the composition (AB) according to the invention, the compound of structure (1) has $R^1$ and $R^2$ being tert-butyl and $R^3$ is —$OCH_2CH_3$, the compound of structure (I) then having structure (XI) (hereinafter also abbreviated as "QM-6")

QM-6

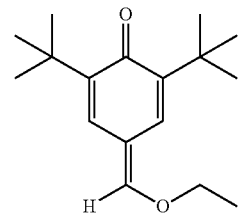

(XI)

and the cyclopentadiene compound is selected from the group consisting of cyclopentadiene, dicyclopentadiene, alkylated cyclopentadiene and alkylated dicyclopentadiene, more preferably selected from the group consisting of cyclopentadiene and dicyclopentadiene.

In an eighth very particularly preferred embodiment of the composition (AB) according to the invention, the compound of structure (I) has $R^1$ and $R^2$ being tert-butyl and $R^3$ is —$OCH_2CH_2CH_3$, the compound of structure (I) then having structure (XII) (hereinafter also abbreviated as "QM-7")

QM-7

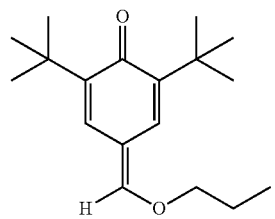

(XII)

and the cyclopentadiene compound is selected from the group consisting of cyclopentadiene, dicyclopentadiene, alkylated cyclopentadiene and alkylated dicyclopentadiene, more preferably selected from the group consisting of cyclopentadiene and dicyclopentadiene.

In a ninth very particularly preferred embodiment of the composition (AB) according to the invention, the compound of structure (I) has $R^1$ and $R^2$ being tert-butyl and $R^3$ is —$OCH(CH_3)_2$, the compound of structure (I) then having structure (XIII) (hereinafter also abbreviated as "QM-8")

QM-8

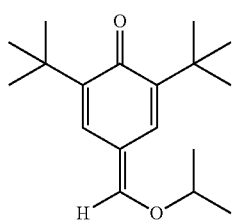

(XIII)

and the cyclopentadiene compound is selected from the group consisting of cyclopentadiene, dicyclopentadiene, alkylated cyclopentadiene and alkylated dicyclopentadiene, more preferably selected from the group consisting of cyclopentadiene and dicyclopentadiene.

In a tenth very particularly preferred embodiment of the composition (AB) according to the invention, the compound of structure (I) has $R^1$ and $R^2$ being tert-butyl and $R^3$ is —OCH$_2$CH$_2$CH$_2$CH$_3$, the compound of structure (I) then having structure (XIV) (hereinafter also abbreviated as "QM-9")

QM-9

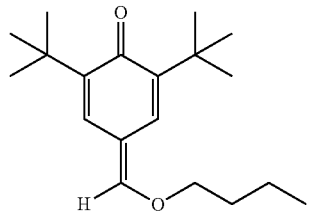

(XIV)

and the cyclopentadiene compound is selected from the group consisting of cyclopentadiene, dicyclopentadiene, alkylated cyclopentadiene and alkylated dicyclopentadiene, more preferably selected from the group consisting of cyclopentadiene and dicyclopentadiene.

In an eleventh very particularly preferred embodiment of the composition (AB) according to the invention, the compound of structure (I) has $R^1$ and $R^2$ being tert-butyl and $R^3$ is —OCH$_2$CH$_2$CH$_2$CH$_2$CH$_3$, the compound of structure (I) then having structure (XV) (hereinafter also abbreviated as "QM-10")

QM-10

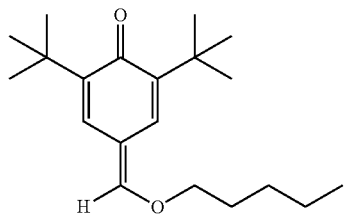

(XV)

and the cyclopentadiene compound is selected from the group consisting of cyclopentadiene, dicyclopentadiene, alkylated cyclopentadiene and alkylated dicyclopentadiene, more preferably selected from the group consisting of cyclopentadiene and dicyclopentadiene.

In a twelfth very particularly preferred embodiment of the composition (AB) according to the invention, the compound of structure (I) has $R^1$ and $R^2$ being tert-butyl and $R^3$ is —OCH$_2$CH$_2$CH$_2$CH$_2$CH$_2$CH$_3$, the compound of structure (I) then having structure (XVI) (hereinafter abbreviated as "QM-11")

QM-11

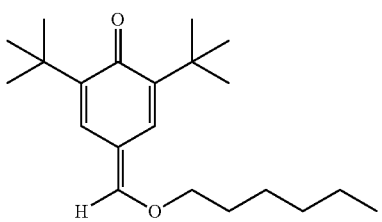

(XVI)

and the cyclopentadiene compound is selected from the group consisting of cyclopentadiene, dicyclopentadiene, alkylated cyclopentadiene and alkylated dicyclopentadiene, more preferably selected from the group consisting of cyclopentadiene and dicyclopentadiene.

In a thirteenth very particularly preferred embodiment of the composition (AB) according to the invention, the compound of structure has (I) has $R^1$ and $R^2$ being tert-butyl and $R^3$ is —C≡C-phenyl, the compound of structure (I) then having structure (XVII) (hereinafter abbreviated as "QM-12")

QM-12

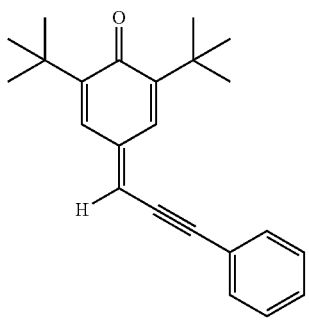

(XVII)

and the cyclopentadiene compound is selected from the group consisting of cyclopentadiene, dicyclopentadiene, alkylated cyclopentadiene and alkylated dicyclopentadiene, more preferably selected from the group consisting of cyclopentadiene and dicyclopentadiene.

In a fourteenth very particularly preferred embodiment of the composition (AB) according to the invention, the compound of structure (I) has $R^1$ and $R^2$ being tert-butyl and $R^3$ is —COOH, the compound of structure (I) then having structure (XVIII) (hereinafter abbreviated as "QM-13")

QM-13

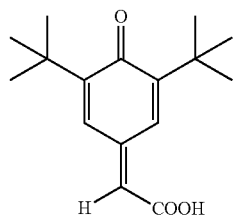

(XVIII)

and the cyclopentadiene compound is selected from the group consisting of cyclopentadiene, dicyclopentadiene, alkylated cyclopentadiene and alkylated dicyclopentadiene, more preferably selected from the group consisting of cyclopentadiene and dicyclopentadiene.

In a fifteenth very particularly preferred embodiment of the composition (AB) according to the invention, the compound of structure (I) has $R^1$ and $R^2$ being tert-butyl and $R^3$ is —SCH$_2$CH$_2$CH$_2$CH$_3$, the compound of structure (I) then having structure (XIX) (hereinafter abbreviated as "QM-14")

QM-14

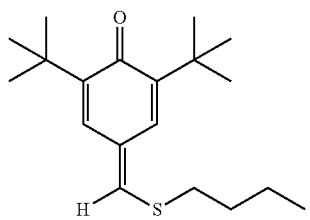

(XIX)

and the cyclopentadiene compound is selected from the group consisting of cyclopentadiene, dicyclopentadiene, alkylated cyclopentadiene and alkylated dicyclopentadiene, more preferably selected from the group consisting of cyclopentadiene and dicyclopentadiene.

In composition (AB) according to the invention, the total concentration of all compounds of structure (I) in said composition (AB) may preferably be between 10 ppb (m/m) and 100,000 ppm (m/m), more preferably between 1 ppm (m/m) and 50,000 ppm (m/m), even more preferably between 10 ppm and 10,000 ppm (m/m), most preferably between 100 ppm and 5000 ppm (m/m), each based on the total weight of all cyclopentadiene compounds in said composition (AB).

Composition (AB) according to the invention in a further preferred embodiment may additionally also comprise (C), where "(C)" has the meaning "at least one solvent".

Any material may be useful as a solvent in the composition (AB) according to the invention provided (A) is soluble therein in the desired concentration range and it is both compatible with (A) and does not have a disruptive effect on the process according to the invention, and is in particular an apolar solvent, preferably an apolar aromatic or aliphatic solvent. It is more preferable for the solvent in the composition (AB) according to the invention to be selected from the group consisting of benzene, mono- or polyalkylated aromatics, alkanes having a carbon number of 6 to 15, cycloalkanes having a carbon number of 6 to 15, high-boiling hydrocarbon cuts, ethers having a carbon number of 6 to 15 and esters having a carbon number of 6 to 15. It is still more preferable for the solvent in the composition (AB) according to the invention to be selected from the group consisting of benzene, toluene, ethylbenzene, xylene, styrene and high-boiling aromatic hydrocarbon cuts. It is particularly preferable for the solvent in the composition (AB) according to the invention to be selected from the group consisting of toluene, ethylbenzene, xylene and styrene. Alternatively, the cyclopentadiene compound itself may also serve as solvent in the composition (AB) according to the invention.

When composition (AB) according to the invention also comprises (C), the (m/m) ratio of the total weight of all compounds of structure (I) which are comprised by composition (AB) to the total weight of all solvents comprised by composition (AB) in composition (AB) may preferably be in the range from 1:1000 to 100:1, more preferably in the range from 1:100 to 10:1 and still more preferably in the range from 1:10 to 3:1.

Use According to the Invention

The expression "use according to the invention" is synonymous with "use of (A) for inhibiting the polymerization of (B)".

The invention also provides for the use of (A) for inhibiting the polymerization of (B), wherein (A) is at least one compound of structure (I)

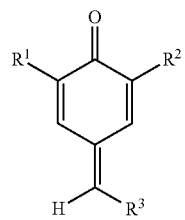

(I)

wherein
  $R^1$ and $R^2$ are each independently hydrogen, alkyl of 1 to 18 carbon atoms, cycloalkyl of 3 to 15 carbon atoms, aryl of 6 to 15 carbon atoms or phenylalkyl of 7 to 15 carbon atoms;
  $R^3$ is —CN, —COOH, —COOR$^4$, —COR$^5$, —OCOR$^6$, —CONR$^7$R$^8$, —PO(OR$^9$)$_2$, —O—R$^{10}$, —S—R$^{11}$, —R$^{12}$, —C≡C—R$^{13}$ or halogen;
wherein
  $R^4$, $R^5$, $R^6$ are alkyl of 1 to 18 carbon atoms, cycloalkyl of 3 to 12 carbon atoms, aryl of 6 to 10 carbon atoms;
  $R^7$ and $R^8$ are each independently hydrogen; alkyl of 1 to 15 carbon atoms which is unsubstituted or substituted with at least one substituent selected from the group consisting of alkylamino having 1 to 4 carbon atoms, dialkylamino having 2 to 8 carbon atoms and hydroxyl; phenylalkyl of 7 to 15 carbon atoms which is unsubstituted or substituted with at least one substituent selected from the group consisting of hydroxyl, alkyl having 1 to 4 carbon atoms, alkylamino having 1 to 4 carbon atoms and dialkylamino having 2 to 8 carbon atoms; aryl of 6 to 10 carbon atoms which is unsubstituted or substituted with at least one substituent selected from the group consisting of alkyl having 1 to 4 carbon atoms, alkylamino having 1 to 4 carbon atoms, dialkylamino having 2 to 8 carbon atoms and hydroxyl;
  or NR$^7$R$^8$ is morpholino, piperidino or pyrrolidino;
  $R^9$, $R^{10}$, $R^{11}$ are hydrogen; alkyl of 1 to 15 carbon atoms which is unsubstituted or substituted with at least one substituent selected from the group consisting of hydroxyl, dialkylamino, —OR$^{14}$, —[O(CH$_2$)$_y$]$_x$H, where x is 1, 2, 3, 4, 5, 6, 7, 8, 9 or 10 and y is 1, 2, 3 or 4 and where R$^{14}$ is alkyl of 1 to 6 carbon atoms; cycloalkyl of 3 to 15 carbon atoms which is unsubstituted or substituted with at least one substituent selected from the group consisting of hydroxyl, dialkylamino, —OR$^{14}$, —[O(CH$_2$)$_y$]$_x$H, where x is 1, 2, 3, 4, 5, 6, 7, 8, 9 or 10 and y is 1, 2, 3 or 4 and where R$^{14}$ is alkyl of 1 to 6 carbon atoms; phenylalkyl of 7 to 15 carbon atoms which is unsubstituted or substituted with at least one substituent selected from the group consisting of hydroxyl, dialkylamino, —OR$^{14}$, —[O(CH$_2$)$_y$]$_x$H, where x is 1, 2, 3, 4, 5, 6, 7, 8, 9 or 10 and y is 1, 2, 3 or 4 and where R$^{14}$ is alkyl of 1 to 6 carbon atoms; or aryl of 6 to 15 carbon atoms which is unsubstituted or substituted with at least one substituent selected from the group consisting of hydroxyl, dialkylamino, —OR$^{14}$, —[O(CH$_2$)$_y$]$_x$H, where x is 1, 2, 3, 4, 5, 6, 7, 8, 9 or 10 and y is 1, 2, 3 or 4 and where R$^{14}$ is alkyl of 1 to 6 carbon atoms;

$R^{12}$ is 2-pyridyl, 3-pyridyl, 4-pyridyl, 2-thienyl, 3-thienyl, 2-pyrryl, 3-pyrryl, 2-furyl, 3-furyl or aryl of 6 to 15 carbon atoms; wherein the radicals 2-pyridyl, 3-pyridyl, 4-pyridyl, 2-thienyl, 3-thienyl, 2-pyrryl, 3-pyrryl, 2-furyl, 3-furyl or aryl of 6 to 15 carbon atoms are unsubstituted or substituted with at least one substituent selected from the group consisting of hydroxyl, nitro, amino, cyano, carboxyl, aminocarbonyl, halogen, alkyl of 1 to 8 carbon atoms, alkoxy of 1 to 8 carbon atoms, alkylthio of 1 to 8 carbon atoms, alkylamino of 1 to 8 carbon atoms, dialkylamino of 2 to 8 carbon atoms and a carboxylic ester group of 2 to 8 carbon atoms;

$R^{13}$ is hydrogen, alkyl of 1 to 12 carbon atoms, aryl of 6 to 10 carbon atoms, wherein the aryl of 6 to 10 carbon atoms is unsubstituted or substituted with at least one substituent selected from the group consisting of hydroxyl, nitro, amino, cyano, carboxyl, aminocarbonyl, halogen, alkyl of 1 to 8 carbon atoms, alkoxy of 1 to 8 carbon atoms, alkylthio of 1 to 8 carbon atoms, alkylamino of 1 to 8 carbon atoms, dialkylamino of 2 to 8 carbon atoms and a carboxylic ester group of 2 to 8 carbon atoms;

wherein the substituents $R^1$, $R^2$ and $R^3$ are the same or different, and (B) is at least one cyclopentadiene compound.

In one preferred embodiment of the use according to the invention, $R^1$ and $R^2$ in the compound of structure (I) are each independently selected from the group consisting of methyl, ethyl, n-propyl, iso-propyl, n-butyl, iso-butyl and tert-butyl; and $R^3$ is —CN, —COOH, —COOR$^4$, —COR$^5$, —OCOR$^6$, —CONR$^7$R$^8$, —PO(OR$^9$)$_2$, —O—R$^{10}$, —S—R$^{11}$, —R$^{12}$—C≡C—R$^{13}$ or halogen;

wherein $R^4$, $R^5$, $R^6$ are alkyl of 1 to 8 carbon atoms or phenyl;
$R^7R^8$ are each independently hydrogen or alkyl of 1 to 4 carbon atoms, or NR$^7$R$^8$ is morpholino or piperidino;
$R^9$, $R^{10}$, $R^{11}$ are alkyl of 1 to 8 carbon atoms or phenyl;
$R^{12}$ is 2-furyl, 3-furyl or aryl of 6 to 15 carbon atoms, wherein the radicals 2-fu 3-furyl or aryl of 6 to 15 carbon atoms are unsubstituted or substituted with at least one substituent selected from the group consisting of hydroxyl and alkyl of 1 to 8 carbon atoms; and
$R^{13}$ is hydrogen, alkyl of 1 to 12 carbon atoms, aryl of 6 to 10 carbon atoms.

In one more preferred embodiment of the use according to the invention, $R^1$ and $R^2$ in the compound of structure (I) are each independently selected from the group consisting of methyl and tert-butyl; and
$R^3$ is —CN, —COOH, —COOR$^4$, —S—R$^{11}$, —R$^{12}$, —C≡C—R$^{13}$ or halogen;
wherein $R^4$ is alkyl of 1 to 4 carbon atoms;
$R^{10}$, $R^{11}$ are alkyl of 1 to 6 carbon atoms;
$R^{12}$ is 2-furyl, 3-furyl or aryl of 6 to 12 carbon atoms, wherein the radicals 2-fu 3-furyl or aryl of 6 to 12 carbon atoms are unsubstituted or substituted with at least one substituent selected from the group consisting of hydroxyl and alkyl of 1 to 8 carbon atoms; and
$R^{13}$ is aryl of 6 to 10 carbon atoms.

In one still more preferred embodiment of the use according to the invention, $R^1$ and $R^2$ are each tert-butyl in the compound of structure (I); and $R^3$ is —CN, —COOH, —O—R$^{10}$, —S—R$^{11}$, —R$^{12}$ or —C≡C—R$^{13}$;
wherein
$R^{10}$ is methyl, ethyl, iso-propyl, n-propyl, n-butyl, iso-butyl, sec-butyl, tert-butyl, n-pentyl, 1-methylbutyl, 2-methylbutyl, 3-methylbutyl, 1,1-dimethylpropyl, 1,2-dimethylpropyl, 2,2-dimethylpropyl, 1-ethylpropyl, n-hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl or 1-ethyl-2-methylpropyl, preferably methyl, ethyl, iso-propyl, n-propyl, sec-butyl, n-butyl, n-pentyl, or n-hexyl;

$R^{11}$ is alkyl of 1 to 6 carbon atoms;
$R^{12}$ is 2-furyl, 3-furyl or phenyl, wherein phenyl is unsubstituted or substituted with at least one substituent selected from the group consisting of hydroxyl and alkyl of 1 to 8 carbon atoms; and
$R^{13}$ is phenyl.

In a first very particularly preferred embodiment of the use according to the invention, the compound of structure (I) has $R^1$ and $R^2$ being tert-butyl and $R^3$ is CN, the compound of structure (I) then having structure (V) (hereinafter also abbreviated as "QM-1")

QM-1

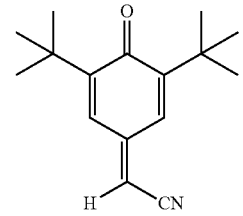

(V)

and the cyclopentadiene compound is selected from the group consisting of cyclopentadiene, dicyclopentadiene, alkylated cyclopentadiene and alkylated dicyclopentadiene, more preferably selected from the group consisting of cyclopentadiene and dicyclopentadiene.

In a second very particularly preferred embodiment of the use according to the invention, the compound of structure (I) has $R^1$ and $R^2$ being tert-butyl and $R^3$ is phenyl, the compound of structure (I) then having structure (VI) (hereinafter also abbreviated as "QM-2")

QM-2

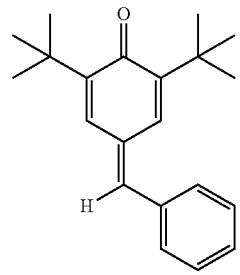

(VI)

and the cyclopentadiene compound is selected from the group consisting of cyclopentadiene, dicyclopentadiene, alkylated cyclopentadiene and alkylated dicyclopentadiene, more preferably selected from the group consisting of cyclopentadiene and dicyclopentadiene.

In a third very particularly preferred embodiment of the use according to the invention, the compound of structure (I)

has $R^1$ and $R^2$ being tert-butyl and $R^3$ is 3,5-di-tert-butyl-4-hydroxyphenyl, the compound of structure (I) then having structure (VII) (hereinafter also abbreviated as "QM-3")

QM3

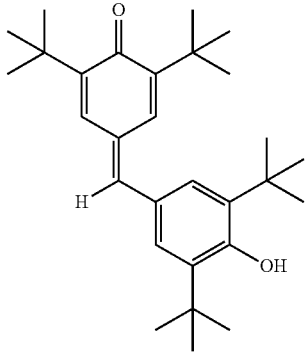

(VII)

and the cyclopentadiene compound is selected from the group consisting of cyclopentadiene, dicyclopentadiene, alkylated cyclopentadiene and alkylated dicyclopentadiene, more preferably selected from the group consisting of cyclopentadiene and dicyclopentadiene.

In a fourth very particularly preferred embodiment of the use according to the invention, the compound of structure (I) has $R^1$ and $R^2$ being tert-butyl and $R^3$ is 2-furyl, the compound of structure (I) then having structure (VIII) (hereinafter also abbreviated as "QM-4")

QM-4

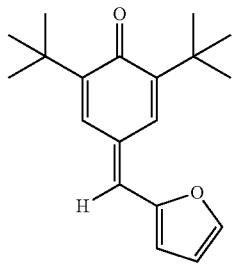

(VIII)

and the cyclopentadiene compound is selected from the group consisting of cyclopentadiene, dicyclopentadiene, alkylated cyclopentadiene and alkylated dicyclopentadiene, more preferably selected from the group consisting of cyclopentadiene and dicyclopentadiene.

In a fifth very particularly preferred embodiment of the use according to the invention, the compound of structure (I) has $R^1$ and $R^2$ being tert-butyl and $R^3$ is —$OR^{10}$, where $R^{10}$ is methyl, ethyl, iso-propyl, n-propyl, n-butyl, sec-butyl, iso-butyl, tert-butyl, n-pentyl, 1-methylbutyl, 2-methylbutyl, 3-methylbutyl, 1,1-dimethylpropyl, 1,2-dimethylpropyl, 2,2-dimethylpropyl, 1-ethylpropyl, n-hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl or 1-ethyl-2-methylpropyl, preferably methyl, ethyl, iso-propyl, n-propyl, n-butyl, sec-butyl, tert-butyl, n-pentyl or n-hexyl, more preferably methyl, ethyl, n-propyl, iso-propyl, n-butyl, n-pentyl or n-hexyl;

the compound of structure (I) then having structure (IX)

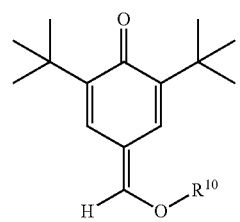

(IX)

and the cyclopentadiene compound is selected from the group consisting of cyclopentadiene, dicyclopentadiene, alkylated cyclopentadiene and alkylated dicyclopentadiene, more preferably selected from the group consisting of cyclopentadiene and dicyclopentadiene.

In a sixth very particularly preferred embodiment of the use according to the invention, the compound of structure (I) has $R^1$ and $R^2$ being tert-butyl and $R^3$=—$OCH_3$, the compound of structure (I) then having structure (X) (hereinafter also abbreviated as "QM-5")

QM-5

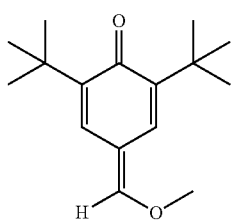

(X)

and the cyclopentadiene compound is selected from the group consisting of cyclopentadiene, dicyclopentadiene, alkylated cyclopentadiene and alkylated dicyclopentadiene, more preferably selected from the group consisting of cyclopentadiene and dicyclopentadiene.

In a seventh very particularly preferred embodiment of the use according to the invention, the compound of structure (I) has $R^1$ and $R^2$ being tert-butyl and $R^3$ is —$OCH_2CH_3$, the compound of structure (I) then having structure (XI) (hereinafter also abbreviated as "QM-6")

QM-6

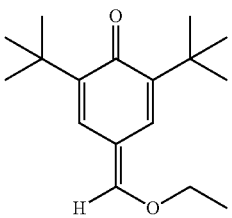

(XI)

and the cyclopentadiene compound is selected from the group consisting of cyclopentadiene, dicyclopentadiene, alkylated cyclopentadiene and alkylated dicyclopentadiene, more preferably selected from the group consisting of cyclopentadiene and dicyclopentadiene.

In an eighth very particularly preferred embodiment of the use according to the invention, the compound of structure (I) has $R^1$ and $R^2$ being tert-butyl and $R^3$ is —OCH$_2$CH$_2$CH$_3$, the compound of structure (I) then having structure (XII) (hereinafter also abbreviated as "QM-7")

QM-7

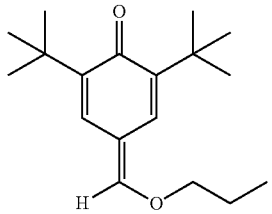

(XII)

and the cyclopentadiene compound is selected from the group consisting of cyclopentadiene, dicyclopentadiene, alkylated cyclopentadiene and alkylated dicyclopentadiene, more preferably selected from the group consisting of cyclopentadiene and dicyclopentadiene.

In a ninth very particularly preferred embodiment of the use according to the invention, the compound of structure (I) has $R^1$ and $R^2$ being tert-butyl and $R^3$ is —OCH(CH$_3$)$_2$, the compound of structure (I) then having structure (XIII) (hereinafter also abbreviated as "QM-8")

QM-8

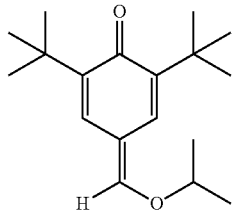

(XIII)

and the cyclopentadiene compound is selected from the group consisting of cyclopentadiene, dicyclopentadiene, alkylated cyclopentadiene and alkylated dicyclopentadiene, more preferably selected from the group consisting of cyclopentadiene and dicyclopentadiene.

In a tenth very particularly preferred embodiment of the use according to the invention, the compound of structure (I) has $R^1$ and $R^2$ being tert-butyl and $R^3$ is —OCH$_2$CH$_2$CH$_2$CH$_3$, the compound of structure (I) then having structure (XIV) (hereinafter also abbreviated as "QM-9")

QM-9

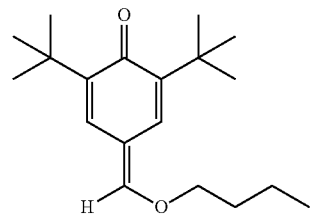

(XIV)

and the cyclopentadiene compound is selected from the group consisting of cyclopentadiene, dicyclopentadiene, alkylated cyclopentadiene and alkylated dicyclopentadiene, more preferably selected from the group consisting of cyclopentadiene and dicyclopentadiene.

In an eleventh very particularly preferred embodiment of the use according to the invention, the compound of structure (I) has $R^1$ and $R^2$ being tert-butyl and $R^3$ is —OCH$_2$CH$_2$CH$_2$CH$_2$CH$_3$, the compound of structure (I) then having structure (XV) (hereinafter also abbreviated as "QM-10")

QM-10

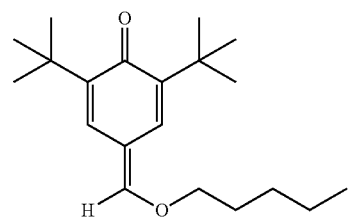

(XV)

and the cyclopentadiene compound is selected from the group consisting of cyclopentadiene, dicyclopentadiene, alkylated cyclopentadiene and alkylated dicyclopentadiene, more preferably selected from the group consisting of cyclopentadiene and dicyclopentadiene.

In a twelfth very particularly preferred embodiment of the use according to the invention, the compound of structure (I) has $R^1$ and $R^2$ being tert-butyl and $R^3$ is —OCH$_2$CH$_2$CH$_2$CH$_2$CH$_2$CH$_3$, the compound of structure (I) then having structure (XVI) (hereinafter abbreviated as "QM-11")

QM-11

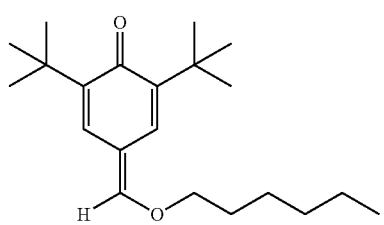

(XVI)

and the cyclopentadiene compound is selected from the group consisting of cyclopentadiene, dicyclopentadiene, alkylated cyclopentadiene and alkylated dicyclopentadiene, more preferably selected from the group consisting of cyclopentadiene and dicyclopentadiene.

In a thirteenth very particularly preferred embodiment of the use according to the invention, the compound of structure (I) has $R^1$ and $R^2$ being tert-butyl and $R^3$ is —C≡C-phenyl, the compound of structure (I) then having structure (XVII) (hereinafter abbreviated as "QM-12")

QM-12

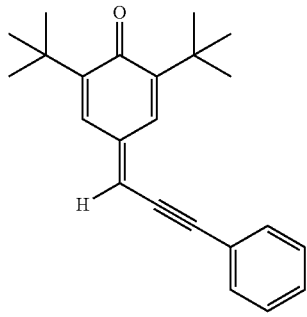

(XVII)

and the cyclopentadiene compound is selected from the group consisting of cyclopentadiene, dicyclopentadiene, alkylated cyclopentadiene and alkylated dicyclopentadiene, more preferably selected from the group consisting of cyclopentadiene and dicyclopentadiene.

In a fourteenth very particularly preferred embodiment of the use according to the invention, the compound of structure (I) has $R^1$ and $R^2$ being tert-butyl and $R^3$ is —COOH, the compound of structure (I) then having structure (XVIII) (hereinafter abbreviated as "QM-13")

QM-13

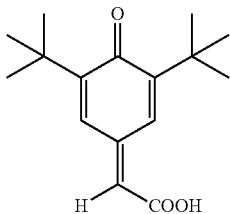

(XVIII)

and the cyclopentadiene compound is selected from the group consisting of cyclopentadiene, dicyclopentadiene, alkylated cyclopentadiene and alkylated dicyclopentadiene, more preferably selected from the group consisting of cyclopentadiene and dicyclopentadiene.

In a fifteenth very particularly preferred embodiment of the use according to the invention, the compound of structure (I) has $R^1$ and $R^2$ being tert-butyl and $R^3$ is —SCH$_2$CH$_2$CH$_2$CH$_3$, the compound of structure (I) then having structure (XIX) (hereinafter abbreviated as "QM-14")

QM-14

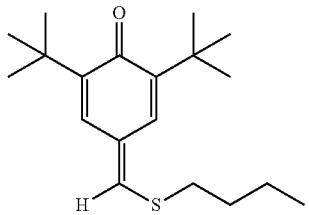

(XIX)

and the cyclopentadiene compound is selected from the group consisting of cyclopentadiene, dicyclopentadiene, alkylated cyclopentadiene and alkylated dicyclopentadiene, more preferably selected from the group consisting of cyclopentadiene and dicyclopentadiene.

(A) may be used in the use according to the invention in gaseous form, as a solid material (as a powder, for example) or as a liquid, in particular as a solid material (as a powder, for example) or as a liquid, preferably as a liquid. (A) used as a liquid in the use according to the invention is more particularly used as a melt or in the form of a solution in (C), where "(C)" has the meaning "at least one solvent".

Any material may be useful as a solvent in the use according to the invention provided (A) is soluble therein in the desired concentration range and it is both compatible with (A) and does not have a disruptive effect on the use according to the invention, and is in particular an apolar solvent, preferably an apolar aromatic or aliphatic solvent. It is more preferable for the solvent in the use according to the invention to be selected from the group consisting of benzene, mono- or polyalkylated aromatics, alkanes having a carbon number of 6 to 15, cycloalkanes having a carbon number of 6 to 15, ethers having a carbon number of 6 to 15, high-boiling hydrocarbon cuts and esters having a carbon number of 6 to 15. It is still more preferable for the solvent in the use according to the invention to be selected from the group consisting of benzene, toluene, ethylbenzene, xylene, styrene and high-boiling aromatic hydrocarbon cuts. It is particularly preferable for the solvent in the use according to the invention to be selected from the group consisting of toluene, ethylbenzene, xylene and styrene. Alternatively, the cyclopentadiene compound itself can also serve as solvent in the use according to the invention.

When (A) is used in the use according to the invention in the form of a solution in (C), the total weight of all compounds of structure (I) in solution (AC) preferably has an (m/m) ratio to the total weight of all solvents in solution (AC) in the range from 1:1000 to 100:1, more preferably in the range from 1:100 to 10:1 and still more preferably in the range from 1:10 to 3:1.

(B) may be present in the use according to the invention in gaseous form, as a liquid or as a solid material, in particular in gaseous form or as a liquid, preferably as a liquid. (B) as a liquid is still more preferably in the form of a melt or solution. It is particularly preferable for (B) to be in the form of a solution. Such a solution in a first very particularly preferred embodiment of the use according to the invention is a process stream as obtained in cracking processes. (B) is typically present in such a process stream at from 0.0001 wt % to 15 wt %.

In an alternative second very particularly preferred embodiment of the use according to the invention, the solution may be a process stream as generated in the production of DCPD and/or CPD itself. (B) is typically present in such a process stream at between 15 and 100 wt %, preferably between 70 and 100 wt % and still more preferably between 70 and 99.99 wt %.

The use according to the invention typically comprises bringing (A) and (B) into contact, which for the purposes of the invention is to be understood as meaning in particular that (A) is admixed to (B) or (B) is admixed to (A).

Admixing (A) to (B) or (B) to (A) can be conducted according to conventionally known methods.

(A) can be admixed with advantage in the use according to the invention into any feedstream or outflow line of a distillation column, into the in- and outflow line of a heat exchanger or into the in- and outflow line of a vaporizer ("reboiler") or into the in- and outflow line of a condenser or into the in- and outflow line of a reactor. (A) can also be added in the use according to the invention to storage tanks containing a process stream comprising (B). (A) can be admixed to (B) not only before but also during a process, for example a production or purification process.

An effective amount of (A) is admixed in the use according to the invention. The term "effective amount of (A)" in the context of this invention is to be understood as meaning the amount of (A) needed to delay/prevent the undesired polymerization of (B). This effective amount depends on the conditions under which the cyclopentadiene compound, or mixture of two or more cyclopentadiene compounds, is stored or handled and may readily be determined from case to case by a person skilled in the art. For example, the cracking of dicyclopentadiene requires by reason of the higher temperatures a higher amount of (A) than the storing of (B) at for instance room temperature.

(A) is preferably used in the use according to the invention in such an amount that the total concentration of all compounds of structure (I) is between 10 ppb (m/m) and 100,000 ppm (m/m), more preferably between 1 ppm (m/m) and 50,000 ppm (m/m), even more preferably between 10 ppm and 10 000 ppm (m/m) most preferably between 100 ppm and 5000 ppm (m/m), each based on the total weight of all cyclopentadiene compounds.

The temperature at which the use according to the invention can be carried out is not subject to any in-principle limitation; on the contrary, it is a feature of the present invention that the use according to the invention can be carried out not only at low but also at high temperatures, in particular in the range from 0° C. to 250° C., preferably 0° C. to 200° C.

The use according to the invention may utilize a polymerization inhibitor (D) as well as (A). Polymerization inhibitors of this type are conventionally known, examples being nitroxides such as, for instance, oxo-TEMPO or 4-hydroxy-TEMPO, phenylenediamines, hydroxylamines such as diethylhydroxylamine (DEHA), nitro- or nitrosoaromatics such as DNBP, (di)phenols such as hydroquinone, TBC or 2,6-di-tert-butylphenol, benzoquinones, phenothiazines such as PTZ.

Having generally described this invention, a further understanding can be obtained by reference to certain specific examples, which are provided herein for purposes of illustration only, and are not intended to be limiting unless otherwise specified.

The examples which follow shall further elucidate the invention without the invention being limited to these embodiments.

EXAMPLES

General Description—Screening Test; Examples 1-11

The following apparatus was set up: A 250 mL multi-neck flask was fitted with a reflux condenser, a nitrogen supply and a sampler.

A 100 g quantity of dicyclopentadiene (purity: 98%) was melted and weighed into the 250 mL flask.

Nitrogen was passed over the dicyclopentadiene, and 50 mg (500 ppm) of the in-test inhibitor shown in Table 1 are added.

While the flow of nitrogen over the dicyclopentadiene was continued, the flask was immersed in a preheated oil bath at 170° C. As the flask was immersed, the reaction started.

Beginning with the immersion of the flask, 0.5-1 mL samples were taken every 30 minutes with a glass syringe. The samples were diluted in a 1:9 weight ratio in ethylbenzene and measured using an evaporative light scattering (ELS) detector.

The ELS detector (Polymerlabs; model: PL-ELS 1000) was connected to an HPLC system which was operated without separation column. Ethylbenzene was used as the mobile phase at a flow rate of 1 mL/min. The injection volume of the diluted sample is 20 μL.

The ELS detector was set to the following parameters:
nitrogen stream: 1.2 l/h
nebulizer: 100° C.
evaporator: 130° C.

The peak area detected was a measure of the oligomer/polymer content of the sample. The oligomer/polymer contents determined are not absolute. The peak area was proportional to the oligomer/polymer content in the measured region, so the results of the various inhibitors are comparable.

The results after 120 min and 240 min are summarized below in Table 1—and all measured values are depicted in graphical form in FIG. 1.

Example 1 is the blank (without admixture of an inhibitor). Examples 2 to 6 are comparative examples, not in accordance with the invention, which were carried out with conventionally known cyclopentadiene polymerization inhibitors 4-hydroxy-TEMPO (4-HT; Example 2), 4-butoxy-TEMPO (4-BT; Example 3), tert-butylcatechol (TBC; Example 4) and dinitro-sec-butylphenol (DNBP; Example 5), hydroquinone monomethyl ether (MeHQ; Example 6). Examples 7 to 11 are examples in accordance with the invention which were carried out with the compounds QM-1 (Example 7), QM-2 (Example 8), QM-5 (Example 9), QM-7 (Example 10) and QM-11 (Example 11).

TABLE 1

| | | Peak area | |
|---|---|---|---|
| Example | Name and structure of inhibitor | after 120 min | after 240 min |
| 1 | no inhibitor (blank) | 1100 | 2300 |
| 2 | 4-hydroxy-TEMPO | 810 | 1880 |

TABLE 1-continued
| Example | Name and structure of inhibitor | Peak area after 120 min | after 240 min |
|---|---|---|---|
| 3 | 4-butoxy-TEMPO 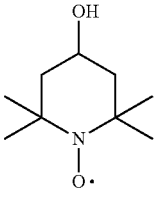 | 750 | 1830 |
| 4 | TBC 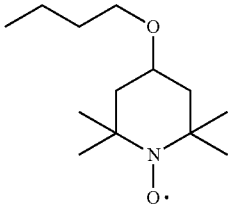 | 340 | 930 |
| 5 | DNBP 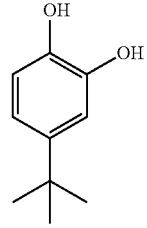 | 1140 | 2450 |
| 6 | MeHQ 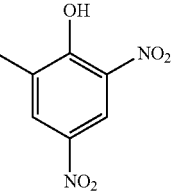 | 1110 | 2350 |
| 7 | QM-1 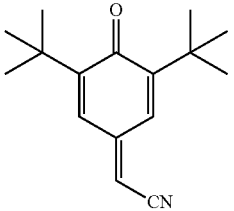 [SMILES: CC(C)(C)C1=CC(=CC#N)C=C(C(C)(C)C)C1=O] | 90 | 320 |

TABLE 1-continued

| Example | Name and structure of inhibitor | Peak area after 120 min | after 240 min |
|---|---|---|---|
| 8 | QM-2 | 160 | 290 |
| 9 | QM-5 | 160 | 360 |
| 10 | QM-7 | 200 | 450 |
| 11 | QM-11 | 330 | 660 |

Results Regarding Examples 1-11:

Example 1 (Comparative Example, not in Accordance with the Invention)

Blank Value (without Inhibitor Admixture)

The curve slopes up continuously over the measurement period of 4 hours, i.e. the polymer content increased continuously. Peak area was 1100 when measured after two hours, slightly more than doubling to 2300 after four hours.

Examples 2 & 3 (Comparative Examples, not in Accordance with the Invention)

TEMPO Derivatives (4-Hydroxy-TEMPO; 4-Butoxy-TEMPO)

The curve in FIG. 1 shows that almost no polymer formed in the first 30 minutes, but thereafter the curves (and hence the polymer content) slope up at the same slope as the curve of the blank test. A peak area of 1400-1700 was attained in this way after four hours.

Example 4 (Comparative Example, not in Accordance with the Invention)

TBC

Polymerization was slowed greatly compared with the blank, the TEMPO derivatives and/or DNBP. Peak area even after four hours is just 640.

Example 5 (Comparative Example, not in Accordance with the Invention)

DNBP

DNBP is a good retarder with "normal" polymerization-prone vinyl-containing monomers, e.g. styrene (see Example 16, not in accordance with the invention). DNBP is likewise reputed to intervene in the Diels-Alder mechanism. DNBP should therefore have been expected to do well in this test. Yet, when used in the test, DNBP was found to have no effect in relation to the polymerization of cyclopentadiene or dicyclopentadiene. Polymerization proceeded in the presence of DNBP in exactly the same way as without any admixture. Detected peak area after two and/or four hours corresponded to that of the blank value (Example 1).

Example 6 (Comparative Example, not in Accordance with the Invention)

MeHQ

MeHQ was used as stabilizer in some of the processes described in the literature. Yet tested with (di-)cyclopentadiene it showed no effect.

Examples 7-11 (Examples in Accordance with the Invention)

Quinone Methides [QM-1, QM-2, QM-5, QM-7, QM-11]

The quinone methides tested are good retarders—as good as DNBP—with "normal" polymerization-prone vinyl-containing monomers, e.g. styrene. Based on conventional wisdom as reported in the literature DNBP v. quinone methides in styrene—quinone methides would therefore not be expected to show any activity.

It was all the more astonishing that the quinone methides used have a very substantial slowing effect on the polymerization of cyclopentadiene/dicyclopentadiene. The effect was greater than that of any other of the inhibitors tested.

Comparative Test with Styrene Monomer; Examples 12-21:

Commercially available stabilized styrene was freed of the stabilizer tert-butyl-1,2-hydroxybenzene (TBC) in an inert nitrogen atmosphere at a reduced pressure of 95 mbar and a pot temperature of 75° C. The experimental apparatus, which consisted of a multi-neck flask equipped with a thermometer, a reflux condenser, a septum and a KPG stirrer, was thoroughly purged with nitrogen to obtain an oxygen-free atmosphere. 300 g of the unstabilized styrene were introduced into the multi-neck flask and admixed with 100 ppm of an inhibitor as per Table 2. A constant supply of nitrogen into the styrene solution through a glass frit ensured an inert nitrogen atmosphere throughout the entire duration of the experiment. The styrene solution was vigorously stirred.

At the start of the experiment, the flask was immersed in a preheated oil bath at 110° C. to such an extent that the stabilized styrene solution is completely immersed. After the three-neck flask had been immersed in the heated oil bath, about 3 g of the styrene solution were removed via the septum at regular intervals, accurately weighed and introduced into 50 ml of methanol. The methanol mixture was stirred at room temperature for half an hour. The methanol worked to precipitate the polystyrene formed during the experiment. This polystyrene was separated off by filtration through a glass filter crucible. The filter residue was washed with 20 ml of methanol and then dried at 110° C. for not less than 5 hours. The polystyrene remaining behind in the glass filter crucible was then weighed. The value found and the initial weight were used to determine the percentage fraction of polymer. This polymer content was plotted against the reaction time (cf. also further values depicted in FIG. 2).

TABLE 2

| Example | Name and structure of inhibitor | Polymer content in % after 120 min | Polymer content in % after 210 min |
|---|---|---|---|
| 12 | no inhibitor (blank) | 9.3 | 16.4 |
| 13 | 4-hydroxy-TEMPO (4-HT) | 3.0 | 8.2 |
| 14 | 4-butoxy-TEMPO | 2.4 | 8.1 |
| 15 | TBC | 6.0 | 14.2 |
| 16 | DNBP | 1.2 | 2.8 |
| 17 | QM-1 | 0.9 | 10.3 |
| 18 | QM-2 | 1.0 | 2.9 |
| 19 | QM-5 | 1.1 | 2.8 |
| 20 | QM-7 | 2.0 | 3.4 |
| 21 | QM-8 | 2.7 | 5.0 |

Evaluation of Examples 12-21

It is apparent from the table that the TEMPO derivatives (Examples 13 and 14) were effective inhibitors of the polymerization of styrene—for a short time. Thereafter, they were spent and virtually devoid of any further activity. Corresponding results were found in (di)cyclopentadiene (Examples 2 and 3).

TBC (Example 15), however, had virtually no effect in the styrene test, but was found to have fairly good activity in (di)cyclopentadiene (Example 4).

With DNBP (Example 16), the effect was exactly the other way round. While its performance in styrene was virtually equivalent to or even better than that of the quinone methides QM-2, QM-5, QM-7, QM-8 (Examples 18-21), DNBP had no effect in (di)cyclopentadiene (Example 5). Yet all the quinone methides were very active in (di)cyclopentadiene (Examples 7-11). In contrast to the other quinone methides, QM-1 proved to be a potent inhibitor in styrene, but was quick to lose its activity (Example 17). In (di)cyclopentadiene, by contrast, it surprisingly shows very good, sustained activity (Example 7).

Comparing the results of the tests with (di)cyclopentadiene and styrene suggests that different mechanisms are involved in the polymerization of the two unsaturated monomers. The effectiveness of inhibitors cannot be predicted as to between monomers.

Figure 2:
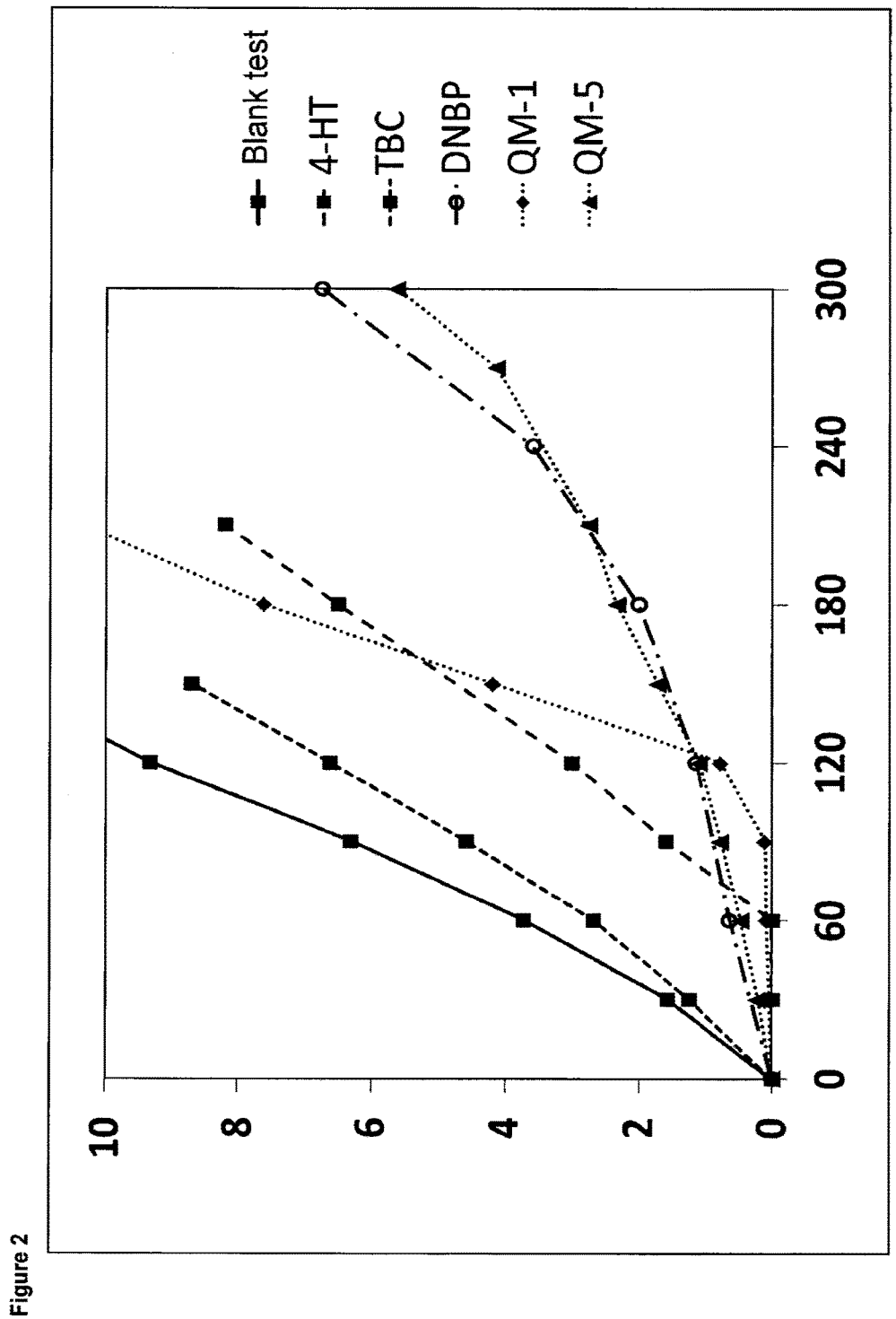
FIG. 2 shows some results obtained in Examples 12 to 21 on comparing certain compounds previously employed and the compounds of the invention in a test of their ability to stabilize styrene against polymerization at 110° C. The x-axis represents the time in minutes, the y-axis the polymer content in %. Further results are found in Table 2. Abbreviations: 4-hydroxy-TEMPO (4-HT), tert-butyl-catechol (TBC) and dinitro-sec-butylphenol (DNBP). The structure of QM-1 is (V), the structure of QM-5 is (X).

The values obtained with QM-1 and QM-5 are shown for comparison in FIG. 2.

General Description—Use in Cyclopentadiene Production; Examples 22 and 23

A 500 ml multi-neck flask was volumetrically calibrated and marked at 400 mL. Continuous metered addition of fresh dicyclopentadiene was provided. The flask was fitted with a heatable column packed with glass Raschig rings. The oil bath was temperature regulated to 180° C.

Technical-grade DCPD (93%) was used in the continuous runs.

The entire dicyclopentadiene to be used was admixed with 5000 ppm of the in-test inhibitor. A slow stream of nitrogen was passed continuously over 100 g of dicyclopentadiene (with inhibitor).

The multi-neck flask was then immersed in the preheated oil bath. Once a pot temperature of 160° C. was reached, 30 ml per hour of dicyclopentadiene (with inhibitor) were metered continuously into the pot. The pot begins to boil at a temperature of about 164° C. and the dicyclopentadiene was cleaved into cyclopentadiene, which distilled over through the column. The cyclopentadiene produced was collected in a receiver cooled to −3° C.

Once insufficient cyclopentadiene was formed under the given temperatures, the pot level rises. When a pot level of 400 mL was reached, the metered addition was terminated and remaining dicyclopentadiene and cyclopentadiene formed was distilled out of the pot. The results are shown in Table 3.

TABLE 3

| Example | Inhibitor | Run time in h | Total amount of DCPD in g | Isolated CPD in g | Yield in % |
|---|---|---|---|---|---|
| 22 | no addition | 38.00 | 1197.2 | 854.8 | 76.8 |
| 23 | QM-5 | 43.50 | 1324 | 976.8 | 79.3 |

The table reveals that the addition of QM-5 had a distinct prolongating effect on the run time in the production of dicyclopentadiene and cyclopentadiene. Instead of for 38 h, the apparatus could be operated for 43.5 h without pot exchange. In addition, the cyclopentadiene yield, based on the entire feed of dicyclopentadiene, went up from 76.8% to 79.3%.

The invention claimed is:

1. A composition (AB), comprising:
a cyclopentadiene compound (B), and
a compound (A) of structure (I):

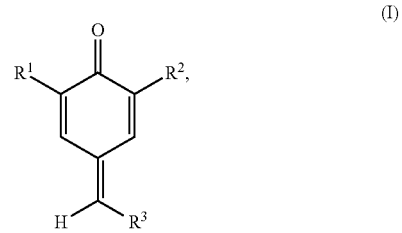

wherein
$R^1$ and $R^2$ are each tert-butyl; and
$R^3$ is —CN, —O—$R^{10}$, or —$R^{12}$, where $R^{10}$ is methyl, ethyl, n-propyl, iso-propyl, n-butyl, n-pentyl, or n-hexyl and $R^{12}$ is 2-furyl, 3-furyl, or phenyl.

2. The composition (AB) according to claim 1, wherein the cyclopentadiene compound (B) is at least one selected from the group consisting of cyclopentadiene, dicyclopentadiene, alkylated cyclopentadiene and alkylated dicyclopentadiene.

3. The composition (AB) according to claim 1, wherein the cyclopentadiene compound (B) is at least one of cyclopentadiene and dicyclopentadiene.

4. The composition (AB) according to claim 1, wherein a concentration of the compound (A) of structure (I) is between 10 ppb (m/m) and 100,000 ppm (m/m), based on a total weight of the cyclopentadiene compound (B).

5. The composition (AB) according to claim 1, wherein, in the structure (I), $R^3$ is —O—$R^{10}$, where $R^{10}$ is methyl.

6. The composition (AB) according to claim 1, wherein, in the structure (I), $R^3$ is —O—$R^{10}$, where $R^{10}$ is ethyl.

7. The composition (AB) according to claim 1, wherein, in the structure (I), $R^3$ is —O—$R^{10}$, where $R^{10}$ is n-propyl.

8. The composition (AB) according to claim 1, wherein, in the structure (I), $R^3$ is —O—$R^{10}$, where $R^{10}$ is iso-propyl.

9. The composition (AB) according to claim 1, wherein, in the structure (I), $R^3$ is —O—$R^{10}$, where $R^{10}$ is n-butyl.

10. The composition (AB) according to claim 1, wherein, in the structure (I), $R^3$ is —O—$R^{10}$, where $R^{10}$ is n-pentyl.

11. The composition (AB) according to claim 1, wherein, in the structure (I), $R^3$ is —O—$R^{10}$, where $R^{10}$ is n-hexyl.

12. The composition (AB) according to claim 1, wherein, in the structure (I), $R^3$ is —$R^{12}$, where $R^{12}$ is 2-furyl.

13. The composition (AB) according to claim 1, wherein, in the structure (I), $R^3$ is —$R^{12}$, where $R^{12}$ is 3-furyl.

14. The composition (AB) according to claim 1, wherein, in the structure (I), $R^3$ is —$R^{12}$, where $R^{12}$ is phenyl.

15. The composition (AB) according to claim 1, wherein, in the structure (I), $R^3$ is —CN.

* * * * *